US005672497A

United States Patent [19]

Cox et al.

[11] Patent Number: 5,672,497

[45] Date of Patent: Sep. 30, 1997

[54] METHOD FOR INCREASING THE ANTIBIOTIC-PRODUCING ABILITY OF ANTIBIOTIC-PRODUCING MICROORGANISMS

[75] Inventors: Karen L. Cox, Martinsville; Scott E. Fishman, Carmel; Charles L. Hershberger, New Palestine; Eugene T. Seno, Indianapolis, all of Ind.

[73] Assignee: Eli Lilly and Company, Indianapolis, Ind.

[21] Appl. No.: 575,843

[22] Filed: Dec. 21, 1995

Related U.S. Application Data

[63] Continuation of Ser. No. 198,672, Feb. 17, 1994, abandoned, which is a continuation of Ser. No. 107,232, Jul. 28, 1993, abandoned, which is a continuation of Ser. No. 742,222, Aug. 6, 1991, abandoned, which is a continuation of Ser. No. 351,350, May 12, 1989, abandoned, which is a continuation-in-part of Ser. No. 18,237, Feb. 24, 1987, abandoned, which is a continuation-in-part of Ser. No. 890,670, Jul. 25, 1986, abandoned, which is a continuation-in-part of Ser. No. 842,330, Mar. 21, 1986, abandoned.

[51] Int. Cl.[6] .......................... C12N 15/00; C12N 15/09; C07H 21/04

[52] U.S. Cl. ...................... 435/320.1; 536/23.1; 536/23.7

[58] Field of Search ............................. 435/172.3, 320.1; 536/23.1, 23.7

[56] References Cited

PUBLICATIONS

Fishman, S.E. et al., Proc. Natl. Acad. Sci., 84:8248–8242, 1987.

Bibb, J.J. et al. Nature, 274:398–400, 1978.

Bierman, M. et al., Gene 116:43–49, 1992.

Baltz, R.H. and Seno, E.T., Ann. Rev. Microbio., 42:547–574, 1988, p. 554.

Matsushima, P. et al., Mol. Gen. Genet. 206:393–400, 1987.

Matsushima, P. et al., J. Bacteriol. 171:3080–3084, 1989.

Bibb et al. (1984) Gene 30, 157–166.

Hunkapiller (1983) Meth. Enzymol. 91, 227–236.

Latae (1985) J. Mol. Biol. 183, 1–12.

Baltz et al., 1982, Genetics and Biochemistry of Tybsin Production, In: Trends in Antibiotic Research (eds. Umezaw et al., published by the Japan Antibiotics Research Association).

Hopwood et al., 1982, Genetic Engineering vol. 4, Setlow, JK and Hollaender (eds), Plenum Press, N.Y., pp. 119–145.

Matsushima et al., 1985, *J. Bacteriol,* 163:180–185.

*Primary Examiner*—David Guzo
*Assistant Examiner*—William Sandals
*Attorney, Agent, or Firm*—Amy E. Hamilton

[57] ABSTRACT

A method for increasing the antibiotic-producing ability of an antibiotic-producing microbial host cell is disclosed. The method involves transforming an antibiotic-producing microorganism with a recombinant DNA cloning vector that codes for the expression of an antibiotic biosynthetic enzyme or other gene product. The gene preferably codes for a product that is rate-limiting in the antibiotic biosynthetic pathway in Streptomyces. Plasmids that are useful for increasing tylosin production in accordance with the present method include plasmids pHJL280, pHJL284, pHJL309, pHJL311, and pHJL315. The invention further comprises microorganisms transformed with plasmids pHJL280, pHJL284, pHJL309, pHJL311, and pHJL315 and also other microorganisms and vectors used in accordance with the present method.

23 Claims, 7 Drawing Sheets

METHOD FOR INCREASING THE ANTIBIOTIC-PRODUCING ABILITY OF ANTIBIOTIC-PRODUCING MICROORGANISMS

CROSS REFERENCE TO RELATED APPLICATIONS

This application is a continuation of application Ser. No. 08/198,672, filed Feb. 17, 1994, which is a continuation of application Ser. No. 08/107/232, filed on Jul. 28, 1993, which is a continuation of application Ser. No. 07/742,222, filed on Aug. 6, 1991, which is a continuation of application Ser. No. 07/351,350, filed on May 12, 1989, now abandoned, which is a continuation-in-part of application Ser. No. 07/018,237, filed Feb. 24, 1987, now abandoned, which is a continuation-in-part of application Ser. No. 06/890,670, filed Jul. 25, 1986, now abandoned, which is a continuation-in-part of application Ser. No. 06/842,330, filed Mar. 21, 1986, now abandoned.

SUMMARY OF THE INVENTION

The present invention is a novel method for increasing the antibiotic-producing ability of an antibiotic-producing organism. The method involves transforming a microbial host cell with a DNA sequence that codes for the expression of a gene product that is rate-limiting in an antibiotic biosynthetic pathway. The invention further comprises related DNA sequences that code for antibiotic biosynthetic gene products, recombinant DNA expression vectors, and transformed microbial host cells.

The present invention represents an early and significant commercial exploitation of recombinant DNA technology in antibiotic-producing organisms such as streptomycetes. Heretofore, the development and exploitation of recombinant DNA technology has been limited, for the most part, to the expression of specific poly-peptides in *E. coli* and, in some instances, mammalian cells. These advances led to the comparatively simple expression of heterologous gene products such as human insulin A and B chains, human proinsulin, human growth hormone, human protein C, human tissue plasminogen activator, bovine growth hormone, and several other compounds of potential value. In each case, heterologous gene expression is more or less independent and does not interact with, take part in, or modulate operative biosynthetic pathways. Recombinant DNA technology can now be applied to improve selected biosynthetic pathways for the expression of more and increased yields of antibiotics or antimicrobial precursors.

Most recombinant DNA technology applied to streptomycetes and other antibiotic-producing organisms has been limited to the development of cloning vectors. Early attempts include the disclosures of Reusser U.S. Pat. No. 4,332,898 and Manis et al. U.S. Pat. Nos. 4,273,875; 4,332,900; 4,338,400; and 4,340,674. Transformation of streptomycetes was not disclosed or taught in these early references. Improved vectors showing greater potential for use in antibiotic-producing organisms were disclosed by Fayerman et al. in U.S. Pat. No. 4,513,086; Nakatsukasa et al. in U.S. Pat. Nos. 4,513,085 and 4,416,994; Malin et al. in U.S. Pat. No. 4,468,462; PCT International Application WO/79/01169; Bibb et al., 1980, in Nature 284:526; Thompson et al., 1980, in Nature 286:525; Suarez et al., 1980, in Nature 286:527; Malpartida et al., 1984, in Nature 309:462; Hershberger, 1982, in Ann. Reports on Fermentation Processes, 5:101–126 (G. T. Tsao, ed., Academic Press, New York); Hershberger et al., 1983, in Ann. N.Y. Acad. Sci. 413:31–46; and Larson and Hershberger, 1984, in J. Bacteriol. 157:314–317. These improved vectors contain markers that are selectable in streptomycetes, can be used to transform many important Streptomyces strains, and constitute the tools required for conducting more complicated gene cloning experiments.

One such experiment was recently reported by Hopwood et al., 1985, in Nature 314:642. Although Hopwood et al. reported the production of novel hybrid antibiotic pigments, the disclosure does not focus on increasing the antibiotic-producing ability or biosynthetic efficiency of a given host cell but instead describes the transferring of actinorhodin pigment biosynthetic genes from one Streptomyces strain to another.

The present invention is particularly useful in that it allows for the commercial application of recombinant DNA technology to streptomycetes and other antibiotic-producing organisms. Because over half of the clinically important antibiotics are produced by streptomycetes, it is especially desirable to develop methods that are applicable to that industrially important group. The present invention provides such methods and allows for the cloning of genes both for increasing the antibiotic-producing ability as well as for the production of new antibiotics and antibiotic precursors in an antibiotic-producing organism.

For purposes of the present invention as disclosed and claimed herein, the following terms are as defined below.

Antibiotic—a substance produced by a microorganism that, either naturally or with limited chemical modification, inhibits the growth of or kills another microorganism or eukaryotic cell.

Antibiotic Biosynthetic Gene—a DNA segment that encodes an enzymatic activity or encodes a product that regulates expression of an enzymatic activity that is necessary for an enzymatic reaction in the process of converting primary metabolites to antibiotic intermediates, which can also possess antibiotic activity, and then to antibiotics.

Antibiotic Biosynthetic Pathway—the entire set of antibiotic biosynthetic genes and biochemical reactions necessary for the process of converting primary metabolites to antibiotic intermediates and then to antibiotics.

Antibiotic-Producing Microorganism—any organism, including, but not limited to Actinoplanes, Actinomadura, Bacillus, Cephalosporium, Micromonospora, Penicillium, Nocardia, and Streptomyces, that either produces an antibiotic or contains genes that, if expressed, would produce an antibiotic.

Antibiotic Resistance-Conferring Gene—a DNA segment that encodes an activity that confers resistance to an antibiotic.

ApR—the ampicillin-resistant phenotype or gene conferring same.

Host Cell—an organism, including the viable protoplast thereof, that can be transformed with a recombinant DNA cloning vector.

NmR—the neomycin-resistant phenotype or gene conferring same.

Operation of Antibiotic Biosynthetic Pathway—the expression of antibiotic biosynthetic genes and the related biochemical reactions required for the conversion of primary metabolites into antibiotics.

Recombinant DNA Cloning Vector—any selectable and autonomously replicating or chromosomally integrating agent, including but not limited to plasmids and phages, comprising a DNA molecule to which additional DNA can be or has been added.

rep—as used in the Figures herein, a Streptomyces plasmid origin of replication.

Restriction Fragment—any linear DNA generated by the action of one or more restriction enzymes.

Sensitive Host Cell—a host cell, including the viable protoplast thereof, that cannot grow in the presence of a given antibiotic without a DNA segment that confers resistance thereto.

Transcriptional Activating Sequence—any DNA sequence that directs, promotes, or provides for the transcription of DNA into a mRNA transcript.

Transformant—a recipient host cell, including the viable protoplast thereof, that has undergone transformation.

Transformation—the introduction of DNA into a recipient host cell, including the viable protoplast thereof, that changes the genotype of the recipient cell.

Translational Activating Sequence—any DNA sequence that provides for the translation of a mRNA transcript into a peptide or polypeptide.

tsr—the thiostrepton-resistant phenotype or gene conferring same.

DESCRIPTION OF THE FIGURES

The plasmid and chromosomal maps depicted in the Figures are drawn to scale. However, the tylosin biosynthetic genes, although linked, are scattered across a large segment of DNA. Therefore, detailed restriction site mapping data exists only for small regions of the large tylosin biosynthetic gene-containing DNA fragment. The maps do not necessarily provide an exhaustive listing of all the cut sites of a given restriction enzyme. The location of individual genes, represented by line segments on the maps, was determined by deletion mapping and thus only approximates the exact location of a given gene.

DETAILED DESCRIPTION OF THE INVENTION

Figure 1:
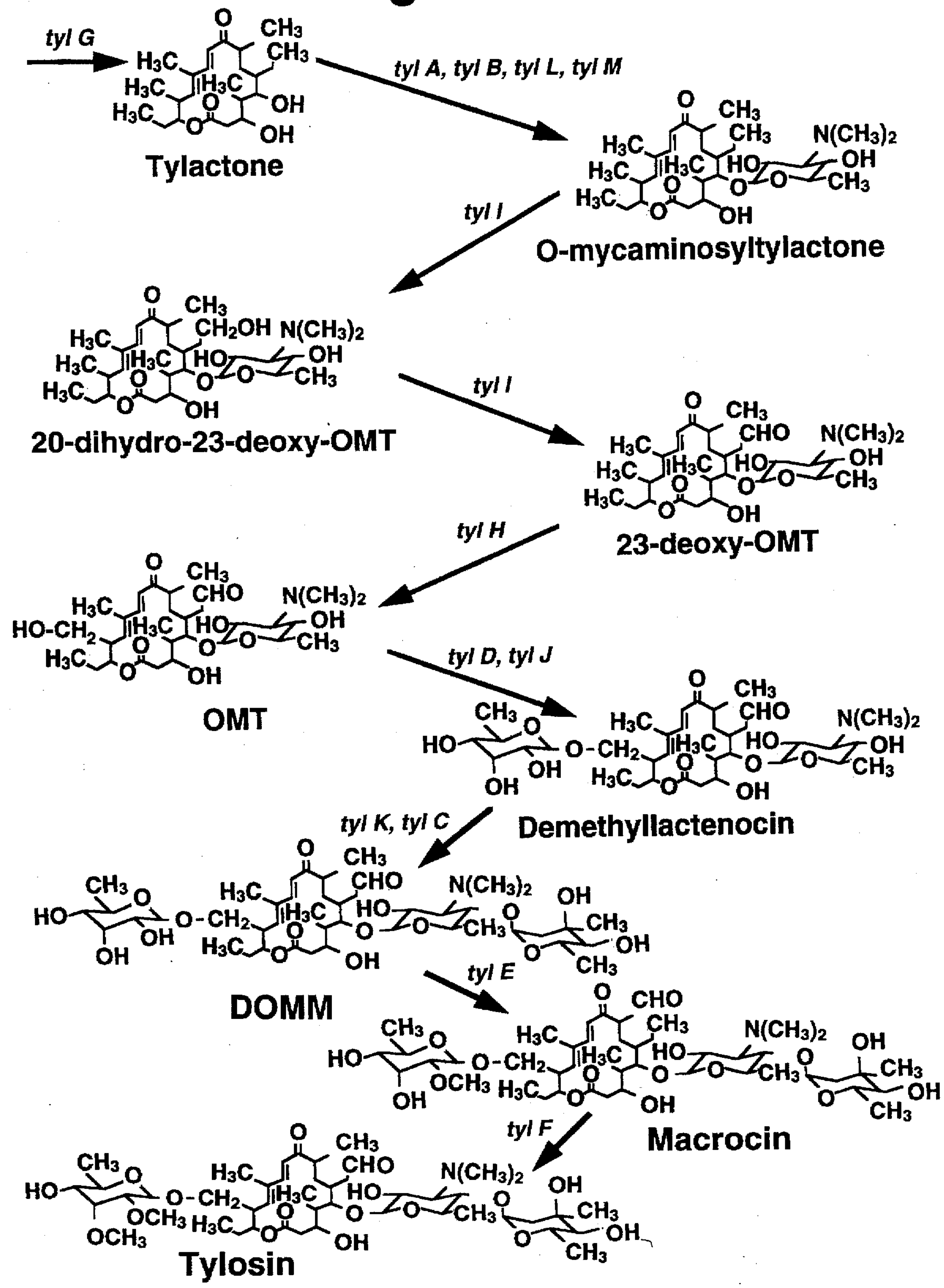
FIG. 1—The Tylosin Biosynthetic Pathway.

The present invention is a method for increasing the antibiotic-producing ability of an antibiotic-producing microorganism, said method comprising 1) transforming a microorganism that produces an antibiotic or antibiotic precursor by means of an antibiotic biosynthetic pathway with a recombinant DNA cloning vector or portion thereof, said vector or portion thereof comprising an antibiotic biosynthetic gene that codes for the expression of an enzyme or other gene product that is rate-limiting in said antibiotic biosynthetic pathway, and 2) culturing said microorganism transformed with said vector under conditions suitable for cell growth, expression of said antibiotic biosynthetic gene, and production of said antibiotic or antibiotic precursor, subject to the limitation that said culturing procedure selected in step (2) provides for an increase in the antibiotic-producing ability of said microorganism.

The invention further comprises related antibiotic biosynthetic genes, recombinant DNA cloning vectors, and antibiotic or antibiotic precursor-producing microorganisms transformed with the aforementioned genes and vectors. The method of the present invention is widely applicable to all antibiotic-producing organisms. The following tables provide a non-exhaustive list of antibiotic producing organisms to which the present invention is applicable.

TABLE I

Aminocyclitol Antibiotic-Producing Organisms

| Organism | Antibiotic |
|---|---|
| Bacillus various species | various aminocyclitols |
| Micromonospora various species | gentamycins |
| Saccharopolyspora various species | various aminocyclitols |
| Streptomyces | |
| *albogriseolus* | neomycins |
| *albus* var. *metamycinus* | metamycin |
| *aquacanus* | N-methyl hygromycin B |
| *atrofaciens* | hygromycins |
| *bikiniensis* | streptomycin |
| *bluensis* var. *bluensis* | bluensomycin |
| *canus* | ribosyl paromamine |
| *catenulae* | catenulin |
| *chrestomyceticus* | aminosidine |
| *crystallinus* | hygromycin A |
| *erythrochromogenes* var. *narutoensis* | streptomycin |
| *eurocidicus* | A16316-C |
| *fradiae* | hybrimycins and neomycins |
| *fradiae* var. *italicus* | aminosidine |
| Streptomyces | |
| *galbus* | streptomycin |
| *griseus* | streptomycin |
| *griseoflavus* | MA 1267 |
| *hofuensis* | seldomycin complex |
| *hygroscopicus* | hygromycins, leucanicidin, and hygrolidin |
| *hygroscopicus* forma *glebosus* | glebomycin |
| *hygroscopicus* var. *limoneus* | validamycins |
| *hygroscopicus* var. *sagamiensis* | spectinomycin |
| *kanamyceticus* | kanamycin A and B |
| *kasugaensis* | kasugamycins |
| *kasugaspinus* | kasugamycins |
| *lavendulae* | neomycin |
| *lividus* | lividomycins |
| *mashuensis* | streptomycin |
| *microsporeus* | SF-767 |
| *netropsis* | LL-AM31 |
| *noboritoensis* | hygromycins |
| *olivaceus* | streptomycin |
| *olivoreticuli* var. *cellulophilus* | destomycin A |
| *poolensis* | streptomycin |
| *rameus* | streptomycin |
| *ribosidificus* | SF733 |
| *rimofaciens* | destomycin A |
| *rimosus* forma *paromomycinus* | paromomycins and catenulin |
| *spectabilis* | spectinomycin |
| *tenebrarius* | tobramycin and |

TABLE I-continued

| Aminocyclitol Antibiotic-Producing Organisms | |
|---|---|
| Organism | Antibiotic |
| | apramycin |
| *Streptoverticillium flavopersicus* | spectinomycin |

TABLE II

| Ansamycin Antibiotic-Producing Organisms | |
|---|---|
| Organism | Antibiotic |
| Micromonospore various species | various ansamycins |
| *Nocardia mediterranei* | rifamycin |
| Streptomyces | |
| *collinus* | ansatrienes and napthomycins |
| *diastochromogenes* | ansatrienes and napthomycins |
| *galbus subsp. griseosporeus* | napthomycin B |
| *hygroscopicus* | herbimycin |
| *hygroscopicus* var. *geldanus* var. *nova* | geldamycin |
| *nigellus* | 21-hydroxy-25-demethyl 25-methylthioproto-streptovaricin |
| *rishiriensis* | mycotrienes |
| sp. E/784 | actamycin and mycotrienes |
| sp. E88 | mycotrienes |
| *spectabilis* | streptovaricins |
| *tolypophorous* | tolypomycin |

TABLE III

| Anthracycline and Quinone Antibiotic-Producing Organisms | |
|---|---|
| Organism | Antibiotic |
| Streptomyces | |
| *caespitosus* | mitomycins A, B, and C |
| *coelicolor* | actinorhodin |
| *coeruleorubidicus* | daunomycin |
| *cyaneus* | ditrisarubicin |
| *flavogriseus* | cyanocycline A |
| *galilaeus* | aclacinomycin A, auramycins, and sulfurmycins |
| *lusitanus* | napthyridinomycin |
| *peuceticus* | daunomycin and adriamycin |
| *violochromogenes* | arugomycin |

TABLE IV

| β-Lactam Antibiotic-Producing Organisms | |
|---|---|
| Organism | Antibiotic |
| Agrobacterium | various β-lactams |
| *Cephalosporium acremonium* | penicillins and cephalosporins |
| Chromobacterium | various β-lactams |
| Gluconobacter | various β-lactams |
| Nocardia | |
| *lactamadurans* | cephamycin C |
| *uniformis* | nocardicin |
| *Penicillium chrysogenum* | various penicillins and other β-lactams |
| Serratia | various β-lactams |
| *antibioticus* | clavulanic acid |
| *argenteolus* | asparenomycin A, MM 4550, and MM 13902 |
| *cattleya* | thienamycin |
| *chartreusis* | SF 1623 and cephamycin A and B |
| Streptomyces | |
| *cinnamonensis* | cephamycin A and B |
| *clavuligerus* | PA-32413-I, cephamycin C, A16886A, penicillins cephalosporins, clavulanic acid, and other clavams |
| *fimbriatus* | cephamycin A and B |
| *flavovirens* | MM 4550 and MM 13902 |
| *flavus* | MM 4550 and MM 13902 |
| *fulvoviridis* | MM 4550 and MM 13902 |
| *griseus* | cephamycin A and B and carpetimycin A and B |
| *halstedi* | cephamycin A and B |
| *heteromorphus* | C2081X and cephamycin A and B |
| *hygroscopicus* | deacetoxycephalosporin C |
| *lipmanii* | cephamycin, penicillin N, 7-methoxycephalosporin C, A16884, MM4550, MM13902 |
| *olivaceus* | epithienamycin F, MM 4550, and MM 13902 |
| *panayensis* | C2081X and cephamycin A and B |
| *rochei* | cephamycin A and B |
| *sioyaensis* | MM 4550 and MM 13902 |
| sp. OA-6129 | OA-6192A |
| sp. KC-6643 | carpetimycin A |
| *viridochromogenes* | cephamycin A and B |
| *wadayamensis* | WS-3442-D |

TABLE V

| Macrolide, Lincosamide, and Streptogramin Antibiotic-Producing Organisms | |
|---|---|
| Organism | Antibiotic |
| *Micromonospore rosaria* | rosaramicin |
| Streptomyces | |
| *albireticuli* | carbomycin |
| *albogriseolus* | mikonomycin |
| *albus* | albomycetin |
| *albus* var. *coilmyceticus* | coleimycin |
| *ambofaciens* | spiramycin and foromacidin D |
| *antibioticus* | oleandomycin |
| *avermitilis* | avermectins |
| *bikiniensis* | chalcomycin |
| *bruneogriseus* | albocycline |
| *caelestis* | M188 and celesticetin |
| *cinerochromogenes* | cineromycin B |
| *cirratus* | cirramycin |
| *deltae* | deltamycins |
| *djakartensis* | niddamycin |
| *erythreus* | erythromycins |
| *eurocidicus* | methymycin |
| *eurythermus* | angolamycin |

TABLE V-continued

| Macrolide, Lincosamide, and Streptogramin Antibiotic-Producing Organisms | |
|---|---|
| Organism | Antibiotic |
| *fasciculus* | amaromycin |
| Streptomyces | |
| *felleus* | argomycin and picromycin |
| *fimbriatus* | amaromycin |
| *flavochromogenes* | amaromycin and shincomycins |
| *fradiae* | tylosin |
| *fungicidicus* | NA-181 |
| *fungicidicus* var. *espinomyceticus* | espinomycins |
| *furdicidicus* | mydecamycin |
| *goshikiensis* | bandamycin |
| *griseofaciens* | PA133A and B |
| *griseoflavus* | acumycin |
| *griseofuscus* | bundlin |
| *griseolus* | griseomycin |
| *griseospiralis* | relomycin |
| *griseus* | borrelidin |
| *griseus* ssp. *sulphurus* | bafilomycins |
| *halstedi* | carbomycin and leucanicidin |
| *hygroscopicus* | tylosin |
| *hygroscopicus* subsp. *aureolacrimosus* | milbemycins |
| *kitastoensis* | leucomycin $A_3$ and josamycin |
| *lavendulae* | aldgamycin |
| *lincolnensis* | lincomycin |
| *loidensis* | vernamycin A and B |
| *macrosporeus* | carbomycin |
| *maizeus* | ingramycin |
| mycarofaciens | acetyl-leukomycin, and espinomycin |
| *narbonensis* | josamycin and narbomycin |
| *narbonensis* var. *josamyceticus* | leucomycin $A_3$ and josamycin |
| *olivochromogenes* | oleandomycin |
| *platensis* | platenomycin |
| *rimosus* | tylosin and neutramycin |
| *rochei* | lankacidin and borrelidin |
| *rochei* var. *volubilis* | T2636 |
| *roseochromogenes* | albocycline |
| *roseocitreus* | albocycline |
| *spinichromogenes* var. *suragaoensis* | kujimycins |
| *tendae* | carbomycin |
| *thermotolerans* | carbomycin |
| *venezuelae* | methymycins |
| *violaceoniger* | lankacidins and lankamycin |

TABLE VI

| Miscellaneous Antibiotic-Producing Streptomyces | | |
|---|---|---|
| Antibiotic Type | Streptomyces Species | Antibiotic |
| amino acid analogues | sp. | cycloserine |
| cyclopentane ring-containing | *coelicolor* | methylenomycin A |
| | *erythrochromogenes* | sarkomycin |
| | *kasugaensis* | aureothricin and thiolutin |
| | *violaceoruber* | methylenomycin A |
| nitro-containing | *venezuelae* | chloramphenicol |
| polyenes | *griseus* | candicidin |

TABLE VI-continued

| Miscellaneous Antibiotic-Producing Streptomyces | | |
|---|---|---|
| Antibiotic Type | Streptomyces Species | Antibiotic |
| | *nodosus* | amphotericin B |
| | *noursei* | nystatin |
| tetracyclines | *aureofaciens* | tetracycline, chlortetracycline, demethyltetracycline, and demethylchlortetracycline |
| | *rimosus* | oxytetracycline |

TABLE VII

| Nucleoside Antibiotic-Producing Organisms | |
|---|---|
| Organism | Antibiotic |
| *Corynebacterium michiganese* pv. *rathayi* | tunicamycin analogues |
| *Nocardia candidus* | pyrazofurin |
| Streptomyces | |
| *antibioticus* | ara-A |
| *chartreusis* | tunicamycin |
| *griseoflavus* var. *thuringiensis* | streptoviridans |
| *griseolus* | sinefungin |
| *lysosuperificus* | tunicamycin |

TABLE VIII

| Peptide Antibiotic-Producing Organisms | |
|---|---|
| Organism | Antibiotic |
| Actinoplanes | |
| *missouriensis* | actaplanin |
| *teichomyceticus* | teicoplanin |
| Bacillus various species | bacitracin, polymixin, and colistin |
| Nocardia | |
| *candidus* | A-35512 and avoparcin |
| *lurida* | ristocetin |
| *orientalis* | vancomycin |
| Streptomyces | |
| *antibioticus* | actinomycin |
| *aureus* | thiostrepton |
| *canus* | amphomycin |
| *eburosporeus* | LL-AM374 |
| *haranomachiensis* | vancomycin |
| *pristinaespiralis* | pristinamycin |
| *roseosporus* | lipopeptides, such as A21978C |
| *toyocaensis* | A47934 |
| *virginiae* | A41030 |

TABLE IX

| Polyether Antibiotic-Producing Organism | |
|---|---|
| Organism | Antibiotic |
| Actinomadura | |
| various species | various polyethers |

TABLE IX-continued

Polyether Antibiotic-Producing Organism

| Organism | Antibiotic |
|---|---|
| *oligosporus* | A80190 |
| Dactylosporangium various species | various polyethers |
| Nocardia various species | various polyethers |
| Streptomyces | |
| *albus* | A204, A28695A and B, and salinomycin |
| *aureofaciens* | narasin |
| *bobili* | A80438 |
| *cacaoi* var. *asoensis* | lysocellin |
| *chartreusis* | A23187 |
| *cinnamonensis* | monensin |
| *conglobatus* | ionomycin |
| *eurocidicus* var. *asterocidicus* | laidlomycin |
| *flaveolus* | CP38936 |
| *gallinarius* | RP 30504 |
| *griseus* | grisorixin |
| *hygroscopicus* | A218, emericid, DE3936, A120A, A28695A and B, etheromycin, and dianemycin |
| *lasaliensis* | lasalocid |
| *longwoodensis* | lysocellin |
| *mutabilis* | S-11743a |
| *pactum* | A80438 |
| *ribosidificus* | lonomycin |
| *violaceoniger* | nigericin |
| Streptoverticillium various species | polyethers |

The present invention is best exemplified by transforming antibiotic-producing microorganisms with genes that code for enzymes that catalyze chemical reactions governing the conversion of primary metabolites into antibiotics. One such enzyme, macrocin O-methyl-transferase, catalyzes the final step in the biosynthesis of tylosin. Transforming tylosin-producing microorganisms with a macrocin O-methyltransferase-encoding gene, designated herein as tylF, results in an improved tylosin biosynthetic pathway as indicated by increased levels of the tylF gene product in the transformed cells. Accordingly, a further object of the present invention is to provide a method for increasing the tylosin-producing or tylosin precursor-producing ability of a tylosin-producing or tylosin precursor-producing microorganism, such method comprising 1) transforming a microorganism that produces tylosin or a tylosin precursor by means of an antibiotic biosynthetic pathway with a recombinant DNA cloning vector or portion thereof, said vector or portion thereof comprising a tylosin biosynthetic gene that codes for an enzyme or other gene product that is rate-limiting in said biosynthetic pathway; and
2) culturing said microorganism transformed with said vector under conditions suitable for cell growth, expression of said antibiotic biosynthetic gene, and production of tylosin or a tylosin precursor, subject to the limitation that said culturing procedure selected in step (2) provides for an increase in the tylosin-producing or tylosin precursor-producing ability of said microorganism.

The method of the present invention utilizes antibiotic biosynthetic genes to increase the antibiotic-producing ability of an organism. A small number of antibiotic biosynthetic genes have been cloned, characterized, and described in the relevant literature. Methods for isolating antibiotic biosynthetic genes have been developed, but one especially preferred method is described in Baltz et al., U.S. patent application Ser. No. 742,349, (U.S. Pat. No. 4,935,340) filed Jun. 7, 1985, attorney docket number X-6640, which is incorporated herein by reference. The tylosin antibiotic biosynthetic genes described herein as a specific exemplification of the present method were initially isolated from a λ library constructed in substantial accordance with the procedure described in Fishman et al., 1985, J. Bacteriology 161:199–206.

A schematic representation of the tylosin biosynthetic pathway is presented in FIG. 1; each arrow in FIG. 1 represents a conversion step in the biosynthesis of tylosin that is catalyzed by one or more tylosin biosynthetic gene products, as indicated by the gene name(s) located above each arrow. Each genotypic designation may represent a class of genes that contribute to the same phenotype. A number of expression vectors are used to exemplify the present invention. These vectors comprise one or more tylosin biosynthetic genes and can be obtained from the Northern Regional Research Laboratories (NRRL), Peoria, Ill. 61604. Table X provides a brief description of each of the plasmids used to exemplify the method of the present invention.

TABLE X

Plasmids Comprising Tylosin Biosynthetic Genes

Figure 2:
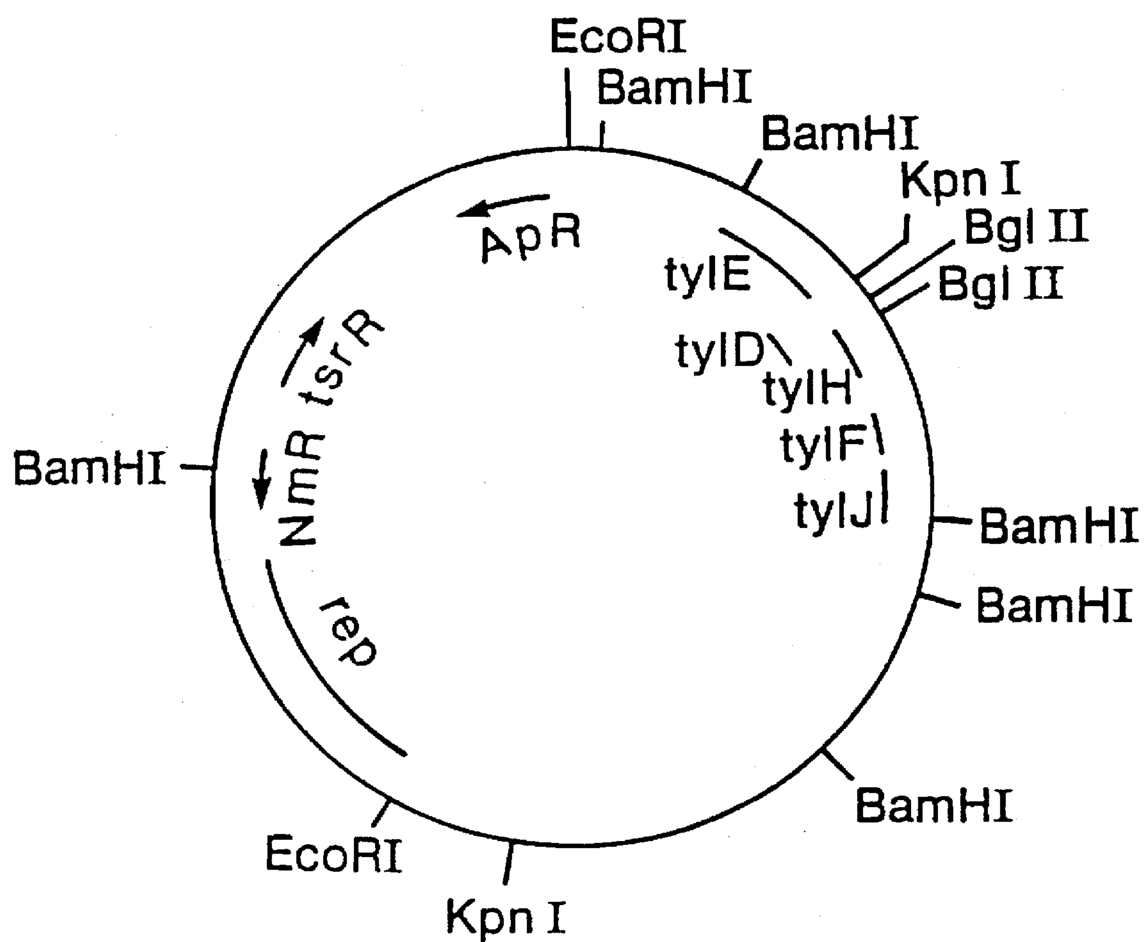
FIG. 2—Restriction Site and Function Map of Plasmid pHJL280.
Figure 3:
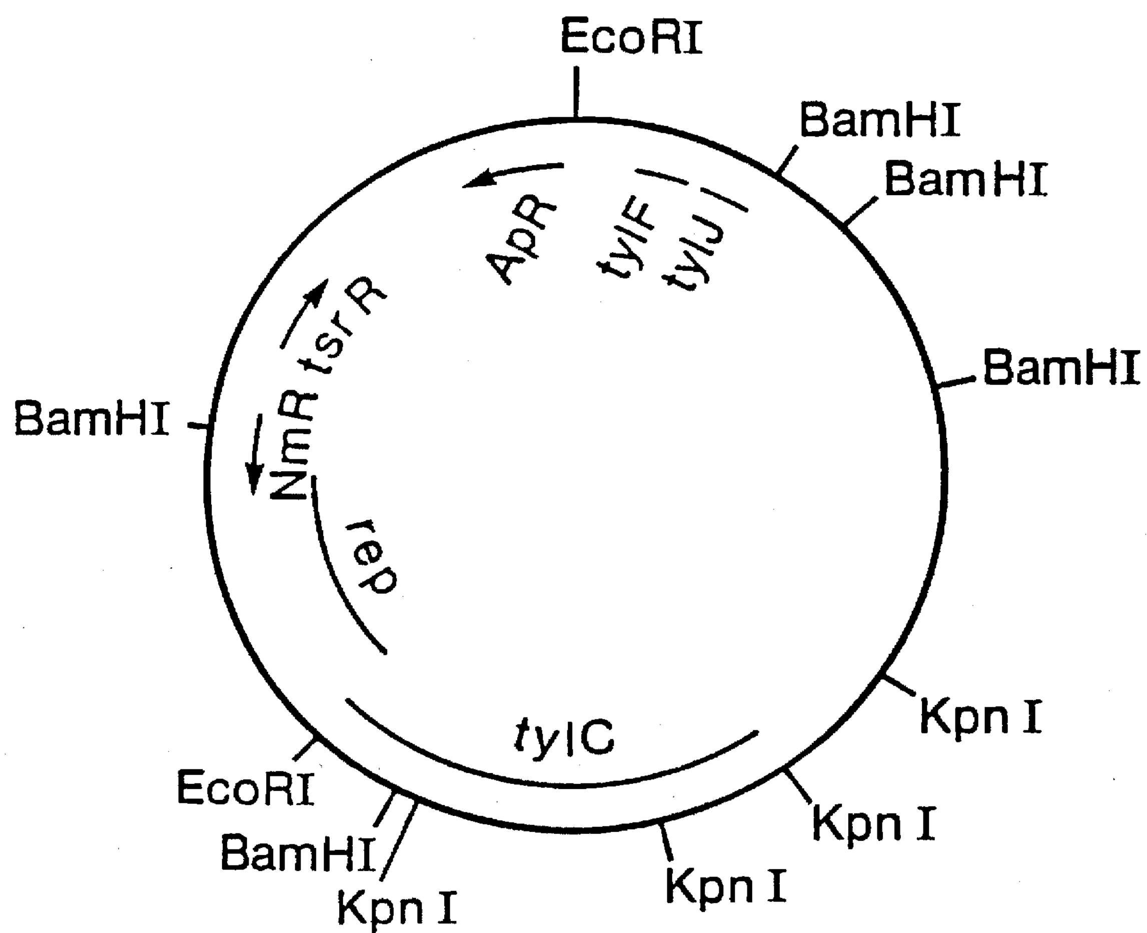
FIG. 3—Restriction Site and Function Map of Plasmid pHJL284.
Figure 4:
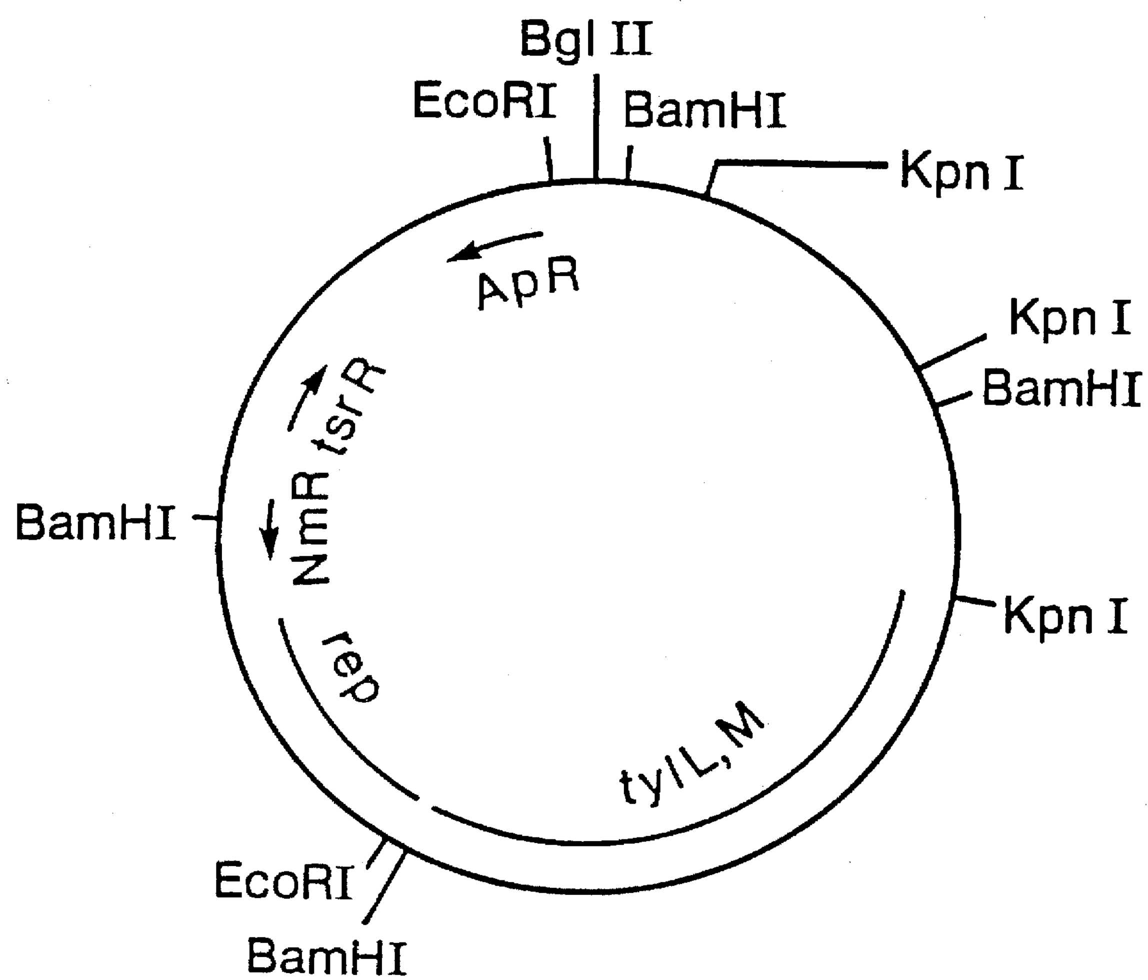
FIG. 4—Restriction Site and Function Map of Plasmid pHJL309.
Figure 5:
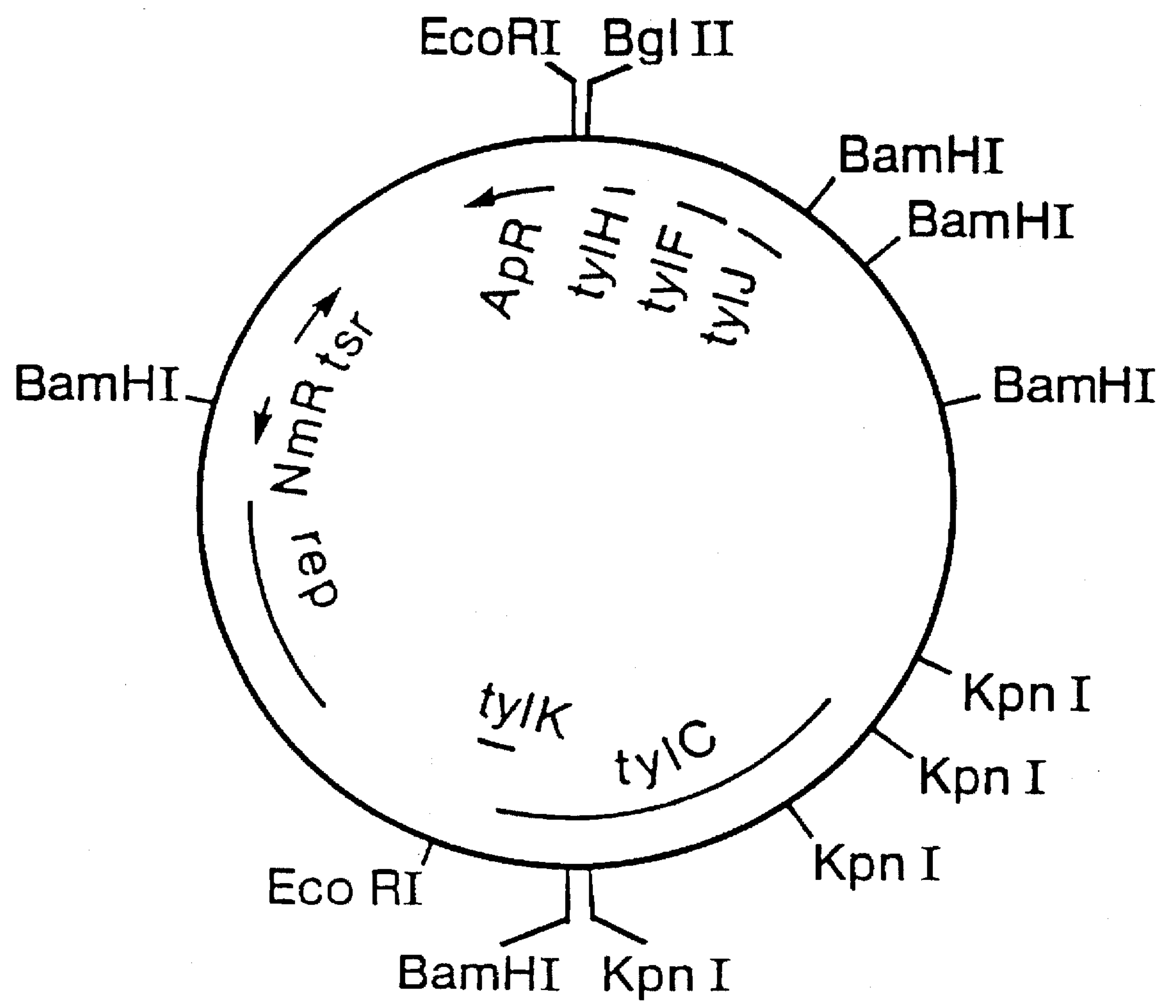
FIG. 5—Restriction Site and Function Map of Plasmid pHJL311.
Figure 6:
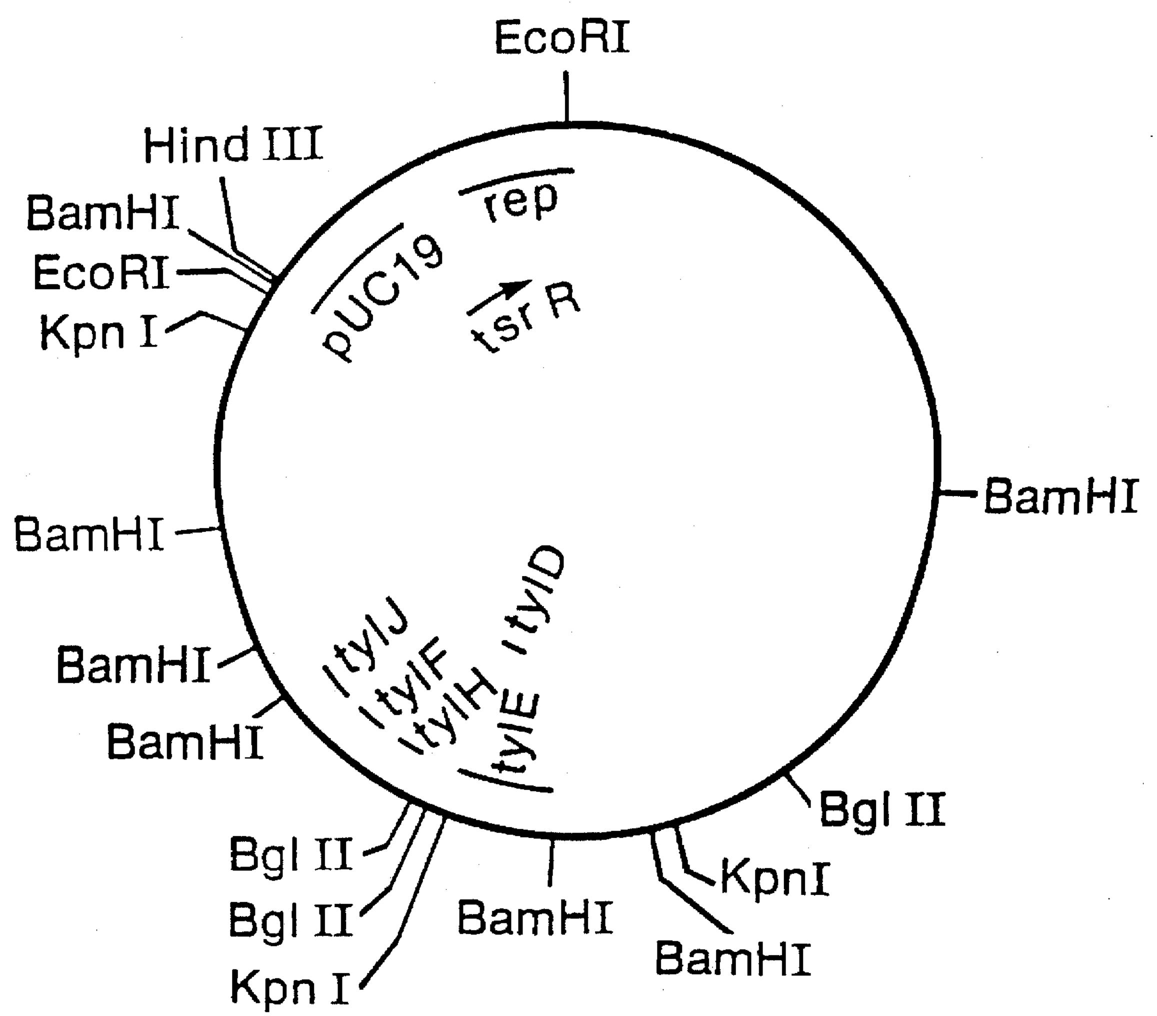
FIG. 6—Restriction Site and Function Map of Plasmid pHJL315.

| Host/Designation | Tylosin Gene(s) | NRRL Accession No. | Map |
|---|---|---|---|
| *E. coli* K12 HB101/pHJL280 | D, E, F, H, J | B-18043 | FIG. 2 |
| *E. coli* K12 HB101/pHJL284 | C, F, J | B-18044 | FIG. 3 |
| *E. coli* K12 HB101/pHJL309 | L, M | B-18045 | FIG. 4 |
| *E. coli* K12 HB101/pHJL311 | C, F, J, K, H | B-18046 | FIG. 5 |
| *E. coli* K12 JM109/pHJL315 | D, E, F, H, J | B-18047 | FIG. 6 |

A number of *Streptomyces fradiae* strains are described herein that have mutant tylosin biosynthetic genes and thus make much less tylosin than the strain from which they were derived. Table XI provides a brief description of these mutant strains.

TABLE XI

*Streptomyces fradiae* Mutants Defective in Tylosin Biosynthesis

| Strain Designation | Mutant Gene | ATCC* or NRRL Accession No. |
|---|---|---|
| GS15 | tylF | NRRL 18058 |
| GS16 | tylE | ATCC 31664 |
| GS28 | tylF | NRRL 18059 |
| GS33 | tylL | |
| GS48 | tylD | NRRL 12170 |
| GS52 | tylC | NRRL 18060 |
| GS62 | tylM | |
| GS76 | tylD<br>tylH | NRRL 12171 |
| GS85 | tylK | |
| GS88 | tylJ | |

*ATCC is the American Type Culture Collection, Rockville, MD 20852, and NRRL is the Northern Regional Research Laboratory, Peoria, IL 61604.

Plasmids pHJL280, pHJL284, and pHJL315 were used to transform *Streptomyces fradiae* GS15 and *Streptomyces fradiae* GS28. The GS15 and GS28 strains were prepared from *S. fradiae* C4 by nitrosoguanidine mutagenesis. *S. fradiae* C4 was derived from *S. fradiae* T59235 (ATCC 19609) by mutagenesis. The GS15 strain makes almost no tylosin, and the GS28 strain makes low levels of tylosin, as compared with the C4 strain. The decreased or nonexistent tylosin-producing ability of the GS15 and GS28 strains is believed to result from mutations affecting the tylF gene, which encodes macrocin O-methyltransferase (MOMT). The MOMT enzyme, which is required for the final conversion of macrocin to tylosin in the tylosin biosynthetic pathway, is frequently present in reaction rate-limiting amounts in tylosin-producing strains. Plasmids pHJL280, pHJL284, and pHJL315 remove this reaction limitation by providing a means for increasing both the copy number of the tylF biosynthetic gene and also the concentration of macrocin O-methyltransferase available for tylosin biosynthesis. Accordingly, fermentation of *S. fradiae* GS15/pHJL280, *S. fradiae* GS15/pHJL284, *S. fradiae* GS15/pHJL315, *S. fradiae* GS28/pHJL284, *S. fradiae* GS28/pHJL280, and *S. fradiae GS*28/pHJL315 for 72 hours results in about a 2-fold to a 6-fold increase in the production of macrocin O-methyltransferase over that produced in the C4 strain and a 120-fold increase over that produced in the GS28 strain.

Plasmid pHJL280 was also used to transform: (1) *Streptomyces fradiae* GS16; (2) *S. fradiae* GS48; (3) *S. fradiae GS*76; and (4) *S. fradiae* GS88 which produce tylosin at levels below the detection limit and were derived by mutagenesis of the C4 strain. Untransformed strains GS16, GS48, GS76, and GS88 respectively produce a defective enzyme or a rate-limiting amount of (1) the tylE, demethylmacrocin O-methyltransferase, enzyme; (2) the tylD enzyme, which is required for addition or biosynthesis of 6-deoxy-D-allose; (3) the tylH enzyme, which is required for oxidation of the C-23 methyl position of tylactone; and (4) the tylJ enzyme. Untransformed strains GS16, GS48, GS76, and GS88 respectively tend to accumulate demethylmacrocin, demycinosyl tylosin, 23-deoxydemycinosyl tylosin, and demycinosyl tylosin rather than the desired tylosin antibiotic compound.

Plasmid pHJL280 provides a means for increasing the efficiency of the tylosin biosynthetic pathway by not only providing a non-defective gene but also by increasing the copy number of the tylD, tylE, tylH, and tylJ biosynthetic genes and by increasing the intracellular amount of the products specified by these genes. The concentration of available tylE gene product is thus increased, resulting in an elevated amount of enzyme capable of driving the conversion of demethylmacrocin to macrocin to tylosin in the tylosin biosynthetic pathway. Similarly, the concentration of available tylD, tylH, and tylJ gene products is also increased, resulting in the production of elevated amounts of the enzymes capable of driving the 6-deoxy-D-allose addition and C-23 oxidation of tylosin precursors. Fermentation of *Streptomyces fradiae* GS16/pHJL280, *S. fradiae GS*48/pHJL280, *S. fradiae* GS76/pHJL280, and *S. fradiae* GS88/pHJL280 for 144–168 hours results in yields of tylosin that are significantly increased over that of the untransformed, low-tylosin-producing, mutant strains. Such transformed strains have higher enzyme levels of the particular enzymes encoded on plasmid pHJL280 than the parent C4 strain and thus further exemplify the present invention. Plasmid pHJL280 can be used to improve the tylosin-producing ability of any organism in which the tylD, tylE, tylF, tylH, or tylJ gene products (or any combination thereof) are present in rate-limiting amounts for tylosin biosynthesis.

Plasmid pHJL284 was also used to transform *Streptomyces fradiae* GS52, a low tylosin-producing, mutant strain derived from the C4 strain that produces reaction-limiting amounts of an enzyme required for the biosynthesis or addition of mycarose to de-O-methyllactenocin. Thus, the tylosin biosynthetic pathway of *Streptomyces fradiae* GS52 tends to produce desmycosin rather than the desired tylosin antibiotic compound. Plasmid pHJL284 provides a means for improving the synthetic efficiency of this pathway by providing a non-defective biosynthetic gene and by increasing the copy number of the tylC biosynthetic gene. The concentration of available tylC gene product in the transformed strain is thus increased, resulting in the elevated production of enzyme capable of driving the desired addition reaction. Accordingly, fermentation of *Streptomyces fradiae* GS52/pHJL284 for 144–168 hours results in a level of tylosin production that is significantly increased over that of the untransformed mutant strain and results in higher tylC enzyme levels than those in the parent C4 strain. Plasmid pHJL284 was also used in the present method to improve the tylosin-producing ability of *Streptomyces fradiae* GS88, a tylJ mutant, and thus can also be used in the present method to improve the tylosin-producing ability of any organism in which the tylC, tylF, or tylJ gene products (or any combination thereof) are present in rate-limiting amounts for tylosin biosynthesis.

Plasmid pHJL309 contains the tylL and tylM biosynthetic genes and so was used in the present method to improve the tylosin-producing ability of *Streptomyces fradiae* GS33, a tylL mutant, and GS62, a tylM mutant. Plasmid pHJL309 can also be used in the present method to improve the tylosin-producing ability of any organism in which the tylL or tylM gene products (or both) are present in rate-limiting amounts for tylosin biosynthesis.

Plasmid pHJL311 contains the tylC, tylF, tylH, tylJ, and tylK biosynthetic genes and so was used in the present method to improve the tylosin-producing ability of *Streptomyces fradiae* GS52, a tylC mutant; GS88, a tylJ mutant; GS15 and GS28, both of which are tylF mutants; and GS85, a tylK mutant. Plasmid pHJL311 can also be used in the present method to improve the tylosin-producing ability of any organism in which the tylC, tylF, tylH, tylJ, or tylK gene products (or any combination thereof) are present in rate-limiting amounts for tylosin biosynthesis.

Plasmid pHJL315 contains the tylD, tylE, tylF, tylH, and tylJ biosynthetic genes and so was used in the present method to improve the tylosin-producing ability of *Streptomyces fradiae* GS48, a tylD mutant; GS88, a tulJ mutant; GS16, a tylE mutant; GS76, a tylD, tylH double mutant; and GS15 and GS28, both of which are tylF mutants. Plasmid pHJL315 can also be used in the present method to improve the tylosin-producing ability of any organism in which the tylD, tylE, tylF, tylH, or tylJ gene products (or any combination thereof) are present in rate-limiting amounts for tylosin biosynthesis.

The results described above demonstrate that the vectors of the present invention can increase the antibiotic-producing ability of an antibiotic-producing organism by providing higher enzyme or other gene product levels, as compared to an untransformed organism, of an enzyme or other gene product that is rate-limiting in an antibiotic biosynthetic pathway. However, plasmid maintenance in an antibiotic-producing host cell sometimes requires significant expenditures of the cell's energy, energy that might otherwise be used to produce antibiotic. Thus, certain microorganisms transformed with autonomously replicating vectors actually show a decrease in antibiotic-producing ability, even though the same vectors can increase the antibiotic-producing ability of other organisms. Not wishing the present invention to be bound or limited in any way by theory, this apparent anomaly can be explained by the fact that antibiotics are produced from primary metabolites, such as acetate, propionate, malonyl-CoA, methylmalonyl-CoA, and glucose, by the action of specific enzymes. These enzymes are usually not present during the rapid growth phase of an organism and so do not rob the growing cell of needed compounds. As growth becomes limited by nutritional conditions, antibiotic biosynthetic genes are believed to be activated, causing the synthesis of enzymes that redirect the flow of certain primary metabolites into antibiotic products.

The synthesis of antibiotics is also believed to be a dispensable function in antibiotic-producing organisms, for mutants blocked in the biosynthesis of antibiotics are viable and grow as well as the antibiotic-producing parent. Wild-type strains produce a relatively small amount of antibiotic, which is apparently adequate to provide the organism with a selective advantage.

The development of industrial antibiotic producing strains from natural isolates involves many cycles of mutation and selection for higher antibiotic production. Because the synthesis of antibiotics drains primary metabolites and cellular energy away from growth and maintenance functions, it is believed that selection for higher antibiotic production frequently occurs at the expense of the vitality of the organism. Thus, the generation of high antibiotic-producing strains involves finely balancing the cells nutritional and energy resources between growth-maintenance functions and antibiotic production. As a consequence of this fine-tuning, high-yielding production strains tend to be extremely sensitive to factors that affect cellular physiology. For example, introduction of autonomously-replicating vectors, notably multicopy plasmids, sometimes tends to decrease the antibiotic-producing ability of an organism that normally produces antibiotics at high levels. The mechanism of this inhibition is not clear, but it is thought to occur at an early step in the biosynthesis of the antibiotic, because measurable levels of antibiotic precursors do not accumulate under these conditions. In addition, autonomously replicating vectors may drain pools of precursors for DNA or RNA synthesis or, in high copy number, may titrate DNA binding proteins, such as RNA polymerase, DNA polymerase, polymerase activators, or repressors of gene expression. Another frequent limitation of autonomously replicating vectors is spontaneous loss. Spontaneous loss is especially problematical when the vector reduces growth rate, as frequently occurs. Selection for a resistance marker on the plasmid can ensure the growth of homogeneous, plasmid-containing populations but can also disrupt the fine physiological balance (already mentioned) of an antibiotic fermentation. Selection for unstable plasmids operates by killing or inhibiting the bacteria that lose the plasmid and can result in a reduced growth rate.

The negative effect, sometimes observed, of autonomously replicating vectors on the antibiotic-producing ability of a microorganism is greatest in high-producing strains that are delicately balanced with respect to growth-maintenance functions and antibiotic production. The present invention overcomes this heretofore unrecognized problem of the negative effect of autonomous plasmid replication on high-producing strains by providing methods of culturing the transformed host cell to facilitate identification of transformed cells containing integrated plasmid and, in addition, by providing vectors with features that also facilitate detection of integration. Selecting a culturing procedure that results in integration is important in improving the antibiotic-producing ability of highly selected and conventionally improved antibiotic-producing organisms. Organisms or strains that have a low antibiotic-producing ability can be improved by transformation via either integration or autonomous vector replication. As those skilled in the art of fermentation technology will appreciate, the greatest improvement in antibiotic-producing ability is shown when the present invention is applied to low antibiotic-producing strains.

Integration of plasmid DNA is readily accomplished by transforming a given antibiotic-producing strain or mutant thereof according to standard transformation procedures, selecting or otherwise identifying the transformants, and then culturing the cells under conditions that do not require the presence of plasmid DNA sequences for the host cell to grow and replicate. After several generations under non-selective conditions, certain cells will no longer contain free plasmid DNA, so by selecting for or otherwise identifying plasmid DNA sequences present in the host cell, one can identify host cells in which the plasmid DNA has integrated into the chromosomal (genomic) DNA of the cell. This culturing technique to obtain integration of vector DNA is especially useful when used in conjunction with a vector that is inherently unstable in the transformed host cell, so that culturing without selective pressure to maintain the vector generates segregants that are free of the plasmid. Bibb et al., 1980, Nature 384:526–531, describe a DNA sequence needed for stable inheritance of a vector, and a variety of vectors have been constructed that lack this stability sequence.

For instance, cloning vectors pHJL210 and pHJL401, which were used to construct the plasmids of the present invention, lack this stability sequence. Plasmid pHJL210 is disclosed in U.S. patent application Ser. No. 639,566, filed Aug. 10, 1984, attorney docket No. X-6256, now issued as U.S. Pat. No. 4,753,886 (Jun. 28, 1988), incorporated herein by reference. Plasmid pHJL401 is disclosed in U.S. patent application Ser. No. 841,920, U.S. Pat. No. 4,898,828 filed Mar. 20, 1986, attorney docket No. X-6786A, which is a continuation-in-part of Ser. No. 763,172, filed Aug. 7, 1985, attorney docket No. X-6786. As used herein, "unstable" refers to plasmids that are lost at high frequency by transformed cells only when those cells are cultured in the absence of selective pressure for plasmid maintenance, for plasmids such as pHJL210 and pHJL401 are quite stable when selective pressure is applied to the transformed host cell. When host cells transformed with stable vectors are cultured in the absence of selective pressure, the vector is not lost with the high frequency observed with unstable vectors, and identification of integrants is made difficult by the great number of cells that still contain autonomously replicating plasmid even after growth under nonselective conditions. Selection for integrants is more fully described below. Once the vector DNA has integrated into the chromosomal DNA of the host cell, one observes the maximum increase in antibiotic-producing ability for that host cell, because inhibition by autonomously replicating plasmid no longer occurs.

Integration of vectors containing cloned genes into the genome of the producing organism can be achieved in a number of ways. One way is to use a lysogenic bacteriophage or other phage vector that can integrate into the genome of the host strain. Another approach is to use a plasmid vector carrying the cloned genes and to screen for integration of the recombinant plasmid into the host genome by a single recombination event between the cloned sequence and the homologous chromosomal sequence. Integration frequency of a vector can be dramatically increased by adding DNA homologous to the genomic DNA of the host cell to the vector. As used herein, integration refers both to a single recombination event, known as Campbell-type recombination, and also to a double-crossover event, which results in exchange of genetic information between the vector and the chromosome. With double-crossover recombination, only a portion of the vector integrates into the chromosomal DNA.

For example, a plasmid carrying cloned tylosin biosynthetic genes (tyl) could integrate into the *Streptomyces fradiae* genome by a single crossover between the tyl genes on the plasmid and the homologous tyl genes in the genome. Another option would be to put a non-tyl *S. fradiae* DNA sequence on the plasmid in addition to the cloned tyl genes and to screen for integration at the locus corresponding to the non-tyl sequence. The latter approach avoids the possible mutagenic effects of integration into the tyl sequences, but if double-crossover recombination is desired, the vector should comprise the antibiotic biosynthetic genes flanked by separate sequences of homologous DNA.

To avoid the potentially adverse effects, however remote, of a recombinant plasmid (either autonomously replicating or integrated) on tylosin production, one can make use of the ability of *Streptomyces fradiae* to take up tylosin precursors from the culture medium and convert them to tylosin. In one fermentation of a tylosin-producing strain that had been transformed with plasmid pHJL280 and cultured to obtain integrants, only a subpopulation (~18%) of the cells were thiostrepton resistant, which indicates the presence of plasmid pHJL280 sequences. However, this subpopulation contained multiple copies of the genes for two rate-limiting enzymes, demethylmacrocin-O-methyltransferase (DMOMT) and macrocin-O-methyltransferase (MOMT), and consequently elevated (about 9 fold) levels of the two enzymes, and was able to convert all of the normally accumulated demethylmacrocin and macrocin to tylosin (see Table XV).

Thus, one can develop specific strains of *S. fradiae* containing multiple copies of rate-limiting genes and high enzyme levels to act as converters of accumulated precursors to tylosin. These converter strains can be used in several different ways: (1) the converter strain can be co-inoculated into the fermentor with the normal production strain at a low ratio of converter:producer; (2) the converter strain can be introduced into a production fermentation culture late in the cycle to convert intermediates; (3) the converter strain can be kept in a separate "reactor", to which the fermentation production broth from the producer strain would be added; or (4) the converter strain can be immobilized on a column, and fermentation broth from the producer strain passed through. Those skilled in the art will recognize that having separate production and converting populations eliminates the adverse effects that recombinant plasmids sometimes have on antibiotic production in high antibiotic-producing strains.

Separate populations also eliminate vector stability problems, because the converting strains can be grown in small vessels in which antibiotic selection or some other selection means for maintenance of the plasmid can be carefully regulated and controlled. In essence, the converting strain is a source of enzymes, and the production of these enzymes at high level can be approached in much the same way as production of proteins from recombinant plasmids in *E. coli.*

Of course, antibiotic production is only increased by the method of the present invention when the transforming DNA comprises a gene that encodes the rate-limiting enzyme of the untransformed strain. Various methods for determining the rate-limiting step in the biosynthesis of an antibiotic are known in the art (Seno and Baltz, 1982, Antimicrobial Agents and Chemotherapy 21:758–763), but there is no need to identify the rate-limiting step when the entire set of antibiotic biosynthetic genes are available for introduction into the antibiotic-producing strain. If a rate-limiting enzyme is not known, the antibiotic-producing strain is transformed with the entire set of antibiotic biosynthetic genes, thus ensuring that, no matter what enzyme is rate-limiting, the transformed host cell will have higher levels of the rate-limiting enzyme than the untransformed host cell. Often, however, the rate-limiting enzyme of an antibiotic biosynthesis pathway will be known, and the method of the present invention can be used to increase the antibiotic-producing ability of the organism by transforming the organism with a vector that encodes the rate-limiting antibiotic biosynthetic enzyme.

For instance, the GS15 strain, which produces no readily detectable tylosin (the level of tylosin produced by these cells is below the detection limits for the assay used to determine tylosin levels) and the GS28 strain, which produces very low levels of tylosin, contain tylF mutations, so that it is a relatively simple matter to identify the rate-limiting step in tylosin biosynthesis in these mutant strains. The strain from which the GS15 and GS28 strains were derived, designated *Streptomyces fradiae* C4, produces high levels of tylosin and accumulates relatively large amounts of macrocin, the immediate precursor of tylosin on which the tylF gene product acts to form tylosin. Other *S. fradiae* strains that produce even more tylosin than the C4 strain accumulate even more macrocin than the C4 strain. These observations indicate that the tylF gene product is present in rate-limiting amounts for the biosynthesis of tylosin in high tylosin-producing strains. Transformation of these macrocin-accumulating strains with a vector comprising the tylF gene followed by isolation of those transformants that only contain integrated copies of the vector yields transformants that produce more tylosin than the untransformed cells. The increase in tylosin production observed in these transformants is related to the amount of macrocin that accumulates in the untransformed cells. It will be apparent to those skilled in the art that the transformants produced by the foregoing procedure might still contain rate-limiting amounts of the tylF gene product, in which case a further increase of the tylF copy number would further increase tylosin yield, or the transformed strains might now contain rate-limiting amounts of yet another antibiotic biosynthetic enzyme, the level of which could be made non-rate-limiting by the method of the present invention.

The present invention provides both a method and recombinant DNA cloning vectors for increasing the production of an antibiotic by manipulation of antibiotic biosynthetic pathways. An illustrative antibiotic biosynthetic pathway involves the biosynthesis of tylosin, a complex macrolide produced by strains of *Streptomyces fradiae, Streptomyces rimosus*, and *Streptomyces hygroscopicus*. Tylosin is composed of a 16-member branched lactone (tylonolide) to which three sugars (mycarose, mycaminose, and mycinose) are attached. The lactone is derived from two acetates, five propionates, and a butyrate by condensation of a propionyl-S-coenzyme A molecule with two malonyl-S-coenzyme A molecules, four methylmalonyl-S-coenzyme A molecules, and an ethylmalonyl-S-coenzyme A molecule by a scheme believed analogous to that involved in fatty acid biosynthesis. Lactone forma-tion, sugar biosynthesis/attachment, and the conversion of resultant intermediate compounds to tylosin are catalyzed by a series of gene-encoded enzymes. Cloning genes that code for such enzymes allows for modifying and improving the operational efficiency of the tylosin biosynthetic pathway and thus is illustrative of the present invention.

Illustrative tylosin biosynthetic genes that can be used for purposes of the present invention include, for example, the tylC, tylD, tylE, tylF, tylH, tylJ, tylK, tylL, and tylM, genes. Of this group, the tylF gene is preferred, because the macrocin O-methyltransferase enzyme encoded thereby appears to be rate-limiting in the tylosin biosynthetic pathway of most tylosin-producing strains. Macrocin accumulates to unacceptable levels under conditions of optimum fermentation of *Streptomyces fradiae* because of the rate-limiting steps catalyzed by the tylF gene product. The tylF enzyme catalyzes the conversion of macrocin to tylosin, as depicted in FIG. 1 of the accompanying drawings. Over production of the tylF gene product, macrocin O-methyltransferase, results in the more efficient operation of the tylosin biosynthetic pathway as indicated by increased antibiotic yield and lower cost of fermentation.

Those skilled in the art will recognize that the present invention is not limited to the use of plasmids pHJL280, pHJL284, pHJL309, pHJL311, or pHJL315. The antibiotic biosynthetic genes contained in the aforementioned vectors ~16.4 kb fragment contains the tylF, tylC, and tylJ genes. The ~1.7 kb EcoRI-Bam HI restriction fragment of plasmid pHJL311 comprises the tylK gene. The ~18.5 kb EcoRI restriction fragment, as well as the ~8.3 kb Bam HI-KpnI restriction fragment, of plasmid pHJL309 contains the tylL and tylM genes.

Any of the aforementioned tyl gene-containing fragments can be ligated into other vectors to make vectors useful in the present method. Such other vectors include, for example, those vectors disclosed in U.S. Pat. Nos. 4,468,462; 4,513,086; 4,416,994; 4,503,155; and 4,513,185; and also plasmids pIJ101, pIJ350, pIJ702 (ATCC 39155), SCP2* (NRRL 15041), pHJL192, pHJL197, pHJL198, pHJL210, pHJL211, pHJL400, pHJL401, pHJL302, pIJ922, pIJ903, pIJ941, pIJ940, and pIJ916. These vectors replicate in *Streptomyces fradiae* and other tylosin-producing strains and are thus useful for cloning the present antibiotic biosynthetic genes. The "unstable" vectors described above are preferred when integration of the vector is desired.

Figure 7:
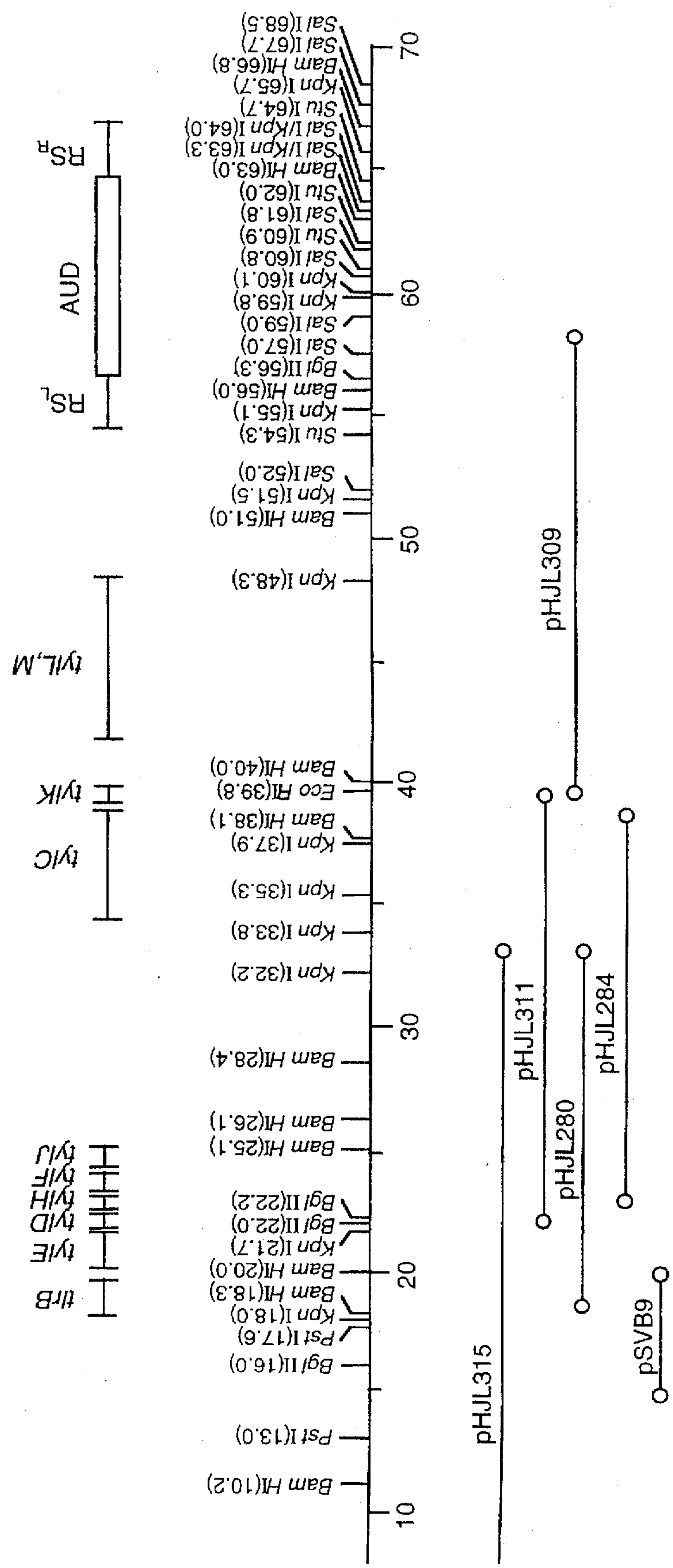
FIG. 7—Chromosomal Organization of the Tylosin Biosynthetic Genes.

A number of tylosin biosynthetic gene-containing vectors have been constructed. Table XII provides a brief description of these plasmids, their construction, and the genes they complement. The tyl gene-containing restriction fragments are identified by their position on the chromosomal map provided in FIG. 7 of the accompanying drawings.

TABLE XII

Tylosin Expressiono Vectors

| | Derivation | | |
|---|---|---|---|
| Vector | Cloning Vector | tyl-containing restriction fragment | Complementation |
| pSKC16 | BamHI-digested pHJL401 | BamHI(20.0)–BamHI(25.1) | E, D, H, F, and J |
| pSKC13 | BamHI-digested pHJL401 | BglII(16.0)–BglII(22.2) | E and D |
| pSFH62 | BamHI-digested pHJL401 | BglII(16.0)–BglII(22.0) | E and D |
| pSFH61 | *EcoRI-HindIII-digested pHJL40-1 | KpnI(18.0)–KpnI(21.7) | E |
| POJ190 | BamHI-KpnI-digested pOJ160** | BamHI(40.0)–KpnI(48.3) | L and M |
| pOJ163 | BamHI-digested pOJ160 | BamHI(40.0)–BamHI(51.0) | L and M |

*The 3.7 KpnI fragment was first cloned into the KpnI site of plasmid pUC19 to yield plasmid pSPH60 which was used as a source of the tylE-containing EcoRI-HindIII fragment.
**Plasmid pOJ160 is available from the NRRL in *E. coli* K12 JM109 under the accession number NRRL B-18088 can be excised in whole or in part and ligated into any number of different recombinant DNA cloning vectors. For instance, digestion of plasmid pHJL280 with restriction enzymes BamHI and BglII yields five Bam HI-BamHI fragments with sizes of ~10.3 kb, ~6.54 kb, ~2.3 kb, ~1.7 kb, and ~1.0 kb; two Bam HI-BglII fragments with sizes of ~2.9 kb and 2.0 kb; and one BglII-BglII fragment ~0.2 kb in size. The ~2.9 kb BamHI-BglII fragment of plasmid pHJL280 contains the tylF gene. Digestion of plasmid pHJL280 with restriction enzymes BglII and EcoRI generates four fragments: an ~11.24 kb EcoRI-EcoRI fragment; an ~11.5 kb BglII-EcoRI fragment; an ~4.0 kb EcoRI-BglII fragment, and an ~0.2 kb BglII-BglII fragment. The ~4.0 kb EcoRI-BglII fragment of plasmid pHJL280 contains the tylE gene.

Digestion of plasmid pHJL28 4 with restriction enzymes BamHI and EcoRI generates three BamHI-BamHI fragments with sizes of ~9.7 kb, ~2.3 kb, and ~1.0 kb; and four EcoRI-BamHI fragments with sizes of ~6.24 kb, ~4.3 kb, ~2.3 kb, and ~1.1 kb. The ~2.3 kb BamHI-EcoRI fragment of plasmid pHJL284 contains the tylF gene. Digestion of plasmid pHJL284 with restriction enzyme EcoRI generates two fragments with sizes of ~16.4 kb and ~10.54 kb; the Illustrative Streptomyces strains that can be used for purposes of the present invention include, for example, *S. fradiae, S. fradiae* GS52, *S. fradiae* GS48, *S. fradiae* GS16, *S. fradiae* GS28, *S. fradiae* GS15, *S. fradiae* GS76, *S. rimosus*, and *S. hygroscopicus. Streptomyces hygroscopicus* and *S. rimosus* are well known, having been deposited at the American Type Culture Collection (ATCC), Rockville, Md. 20852. A number of strains of *S. hygroscopicus* can be obtained under the accession numbers ATCC 27438, ATCC 21449, ATCC 15484, ATCC 19040, and ATCC 15420, and *S. rimosus* can be obtained under the accession number ATCC 10970. Of the Streptomyces taxa, *S. fradiae* GS16, *S. fradiae* GS15, and *S. fradiae* GS28 are preferred, especially for transformation with plasmid pHJL280. *Streptomyces fradiae* is also an especially well known microorganism and several strains are available, on an unrestricted basis, from the Northern Regional Research Laboratory (NRRL), Peoria, Ill. 61604 and the ATCC under the respective accession numbers NRRL 2702, NRRL 2703, and ATCC 19609.

The recombinant plasmids described in the present invention each comprise one or more antibiotic biosynthetic genes. Unless part of a polycistron, each antibiotic biosynthetic gene normally comprises: (1) a promoter (transcriptional activating sequence) that directs transcription of the gene; (2) a sequence that, when transcribed into mRNA, directs translation of the transcript; (3) a protein-coding sequence; and (4) a transcription terminator. Each of these elements is independently useful and can, through the techniques of recombinant DNA technology, be used to form recombinant genes of great variety. As one example, the protein-coding sequence for the tylF gene can be linked to the transcriptional activating sequence, translation-activating sequence, and transcription-terminating sequence from a non-*Streptomyces fradiae* gene to form a recombinant gene that functions in the host from which the non-*S. fradiae* sequences were isolated. Such a novel gene could be used to produce a hybrid antibiotic if introduced into an organism that produced an antibiotic or antibiotic intermediate that is not found in the tylosin pathway but that would serve as a substrate for the novel gene product. Similarly, the promoter and other regulatory elements of the tylF gene could be linked to the coding sequence of a non-tylosin antibiotic biosynthetic gene to prepare a hybrid gene that would function in *S. fradiae*. Thus, the individual elements of each of the antibiotic biosynthetic genes on each of the plasmids described herein comprise an important component of the present invention.

For example, sequence data for the cluster comprised of the tylE, tylD, tylH, tylF, tylJ, as shown below, provides the direction of transcription and translation of each of these genes, possible transcription start sites ("TS"), possible translation-activating sequences ("TAS"), possible transcription end sequences ("TE") and possible translation start sites ("S"). Subscripts associated with these designations indicate for which gene the particular regulatory elements refer. For example, $TS_E$ refers to the transcription start site for the tylE gene. Because the tylE, tylD, tylH, and tylJ genes are transcribed from the complementary strand, both DNA strands of the entire tylEDHFJ cluster, and the projected corresponding amino acid sequence for the proposed coding sequences are provided. Nucleotides designated "N" or "S" indicate that the particular base is not clearly defined. Thus, the sequence for the tylEDHFJ cluster is the following:

```
                                       ********           ********       ********       ********
1    CCCATGGNNAGCAACGCTATSSSSATGGGCCCGCCCCTTCCGCGTGCCCGGGCCCGGTGCCCGTGCCGGGGATCACGCGGCACCGCCCGA   90
     GGGTACCNNTCGTTGCGATASSSSTACCCGGGCGGGGAAGGCGCACGGGCCCGGGCCACGGGCACGGCCCCTAGTGCGCCGTGGCGGGCT
                                       ********           ********       ********       ********  End Ala Ala Gly Gly Ser
                                                                                                  <------ tylE

91   GGAGGCGGCGACCAGGGCGTCGAAGTCCCGCGGGATCCAGCCGGGGATGCCGCCCTCGGAGTTGACCCCCTTCTCGATGAAGGCGAGGTT   180
     CCTCCGCCGCTGGTCCCGCAGCTTCAGGGCGCCCTAGGTCGGCCCCTACGGCGGGAGCCTCAACTGGGGGAAGAGCTACTTCCGCTCCAA
     Ser Ala Ala Val Leu Ala Asp Phe Asp Arg Pro Ile Trp Gly Pro Ile Gly Gly Glu Ser Asn Val Gly Lys Glu Ile Phe Ala Leu Asn
     <----------------------------------------------- tylE -----------------------------------------------

181  GTGGTAAACGTGCAGGCCCACCACGTGGCCGGTCGGCGTAGCCGGGTGAGCGGCCGTGTCCTCGGGGAGTTCCTGGTGCTGGAGGCTGTC   270
     CACCATTTGCACGTCCGGGTGGTGCACCGGCCAGCCGCATCGGCCCACTCGCCGGCACAGGAGCCCCTCAAGGACCACGACCTCCGACAG
     His Tyr Val His Leu Gly Val Val His Gly Thr Pro Thr Ala Pro His Ala Ala Thr Asp Glu Pro Leu Glu Gln His Gln Leu Ser Asp
     <----------------------------------------------- tylE -----------------------------------------------

271  GACGAGTGACTTCACCAGTCCCAGGCTGGTGAGGTCGCTCTTGCCGGGGTCGCTGTCGCCGCCGAAGCCGGGCCAGTAGGCGGTCCACAG   360
     CTGCTCACTGAAGTGGTCAGGGTCCGACCACTCCAGCGAGAACGGCCCCAGCGACAGCGGCGGCTTCGGCCCGGTCATCCGCCAGGTGTC
     Val Leu Ser Lys Val Leu Gly Leu Ser Thr Leu Asp Ser Lys Gly Pro Asp Ser Asp Gly Gly Phe Gly Pro Trp Tyr Ala Thr Trp Leu
     <----------------------------------------------- tylE -----------------------------------------------

361  GTCCTCGATCACATACAGCCCGCCGGGCCGCACATGGGGGAAGAGGGCGTGGAAGGAGGTCCGCACATGCTCGTTGATGTGGCTTCCGTC   450
     CAGGAGCTAGTGTATGTCGGGCGGCCCGGCGTGTACCCCCTTCTCCCGCACCTTCCTCCAGGCGTGTACGAGCAACTACACCGAAGGCAG
     Asp Glu Ile Val Tyr Leu Gly Gly Pro Arg Val His Pro Phe Leu Ala His Phe Ser Thr Arg Val His Glu Asn Ile His Ser Gly Asp
     <----------------------------------------------- tylE -----------------------------------------------

451  GTCGATGACGATGTCGAACGGGCCGTAGCGCGCGGCGAGTTCCGTGAGGCACCCGGGGTCGTTCTGGTCGCCCACCACCGTGGTGATGCG   540
     CAGCTACTGCTACAGCTTGCCCGGCATCGCGCGCCGCTCAAGGCACTCCGTGGGCCCCAGCAAGACCAGCGGGTGGTGGCACCACTACGC
     Asp Ile Val Ile Asp Phe Pro Gly Tyr Arg Ala Ala Leu Glu Thr Leu Cys Gly Pro Asp Asn Gln Asp Gly Val Val Thr Thr Ile Arg
     <----------------------------------------------- tylE -----------------------------------------------

541  CTGTTCCTCGGCGTGTGATTTATCCTCAATGTCCAGGCCGTAGATCAGTCCCCGGTGGAAGAAGTGCTTCCACATGCGCAGTGATCCGCC   630
     GACAAGGAGCCGCACACTAAATAGGAGTTACAGGTCCGGCATCTAGTCAGGGGCCACCTTCTTCACGAAGGTGTACGCGTCACTAGGCGG
     Gln Glu Glu Ala His Ser Lys Asp Glu Ile Asp Leu Gly Tyr Ile Leu Gly Arg His Phe Phe His Lys Trp Met Arg Leu Ser Gly Gly
     <----------------------------------------------- tylE -----------------------------------------------

631  GCCCCACTCGGGGTGCTGGTAGCCGCCTATGCCGATCTCCAGTACCCGCACCTCCTCGTTGCGGTACTCGCGGAAGTGCCGGTCGTAGTG   720
     CGGGGTGAGCCCCACGACCATCGGCGGATACGGCTAGAGGTCATGGGCGTGGAGGAGCAACGCCATGAGCGCCTTCACGGCCAGCATCAC
     Gly Trp Glu Pro His Gln Tyr Gly Gly Ile Gly Ile Glu Leu Val Arg Val Glu Glu Asn Arg Tyr Glu Arg Phr His Arg Asp Tyr His
     <----------------------------------------------- tylE -----------------------------------------------
```

-continued

```
721  CGGAGTGAACCAGTGCAGCGAGCCCCACTTGGGAGTGAGATAGCGCGAGGTGAGTTCGTTCAGGTCCGGTTTGGCCGAGGTGCAGCCCGC  810
     GCCTCACTTGGTCACGTCGCTCGGGGTGAACCCTCACTCTATCGCGCTCCACTCAAGCAAGTCCAGGCCAAACCGGCTCCACGTCGGGCG
     Pro Thr Phe Trp His Leu Ser Gly Trp Lys Pro Thr Leu Tyr Arg Ser Thr Leu Glu Asn Leu Asp Pro Lys Ala Ser Thr Cys Gly Ala
     <---------------------------------- tylE ----------------------------------

811  CAGGACGGTGGCCGTCGCCTGCTGCGCCGCGAGGAAGTAGGTGTCGATGTGGCCGGTGCCGGAGGTGGCGTAGGGGAAGAGGGTGGTTCC  900
     GTCCTGCCACCGGCAGCGGACGACGCGGCGCTCCTTCATCCACAGCTACACCGGCCACGGCCTCCACCGCATCCCCTTCTCCCACCAAGG
     Leu Val Thr Ala Thr Ala Gln Gln Ala Ala Leu Phe Tyr Thr Asp Ile His Gly Thr Gly Ser Thr Ala Tyr Pro Phe Leu Thr Thr Gly
     <---------------------------------- tylE ----------------------------------

901  CCTGGTCCCGGCGGCCCGCTCCCGGCAGGGGCCAAACAACTCCCGTACCAGTTCGTCGAGTTCGTATTCGACGCGCATCGCGACAAAGCC  990
     GGACCAGGGCCGCCGGGCGAGGGCCGTCCCCGGTTTGTTGAGGGCATGGTCAAGCAGCTCAAGCATAAGCTGCGCGTAGCGCTGTTTCGG
     Arg Thr Gly Ala Ala Arg Glu Arg Cys Pro Gly Phe Leu Glu Arg Val Leu Glu Asp Leu Glu Tyr Glu Val Arg Met Ala Val Phe Gly
     <---------------------------------- tylE ----------------------------------

991  GTCGTCATCGGGGGCGGCGCGGCGCACGGGGGCGCCCTGGGCGACCGCCAGCCGCCGCGGCACCAGCGCGTCGCCGGACCGTACGGCGAG  1080
     CAGCAGTAGCCCCCGCCGCGCCGCGTGCCCCCGCGGGACCCGCTGGCGGTCGGCGGCGCCGTGGTCGCGCAGCGGCCTGGCATGCCGCTC
     Asp Asp Asp Pro Ala Ala Arg Arg Val Pro Ala Gly Gln Ala Val Ala Leu Arg Arg Pro Val Leu Ala Asp Gly Ser Arg Val Ala Leu
     <---------------------------------- tylE ----------------------------------

1081 TTCCACCAGTACCGGCACGTCGTTGACCGGGTGCGGCGCCCGGGAGACGATCTCGTCGACCAGGACCGCAGTCACCGCCTCCGGCCCGTG  1170
     AAGGTGGTCATGGCCGTGCAGCAACTGGCCCACGCCGCGGGCCCTCTGCTAGAGCAGCTGGTCCTGGCGTCAGTGGCGGAGGCCGGGCAC
     Glu Val Leu Val Pro Val Asp Asn Val Pro His Pro Ala Arg Ser Val Ile Glu Asp Val Leu Val Ala Thr Val Ala Glu Pro Gly His
     <---------------------------------- tylE ----------------------------------

1171 TTCGGCCACCAGCTCCCGCACATCCGCGGCGTGGCCGCCGGCCGCCCTGATGATCTGCCGCACCAGAGTGGCCTCTTTCTGCACAGCCAT  1260
     AAGCCGGTGGTCGAGGGCGTGTAGGCGCCGCACCGGCGGCCGGCGGGACTACTAGACGGCGTGGTCTCACCGGAGAAAGACGTGTCGGTA
                                                                                            S_E
     Glu Ala Val Leu Glu Arg Val Asp Ala Ala His Gly Gly Ala Ala Arg Ile Ile Gln Arg Val Leu Thr Ala Glu Lys Gln Val Ala Met
     <---------------------------------- tylE ----------------------------------

1261 GTTCTTCCTTCGGGATTCACGAGTGGGGTGCCCGCGACGGCCGGTGGTGTCCGCGGTACCAGCGGATGGTCTGCTCGATCCCCACGCGCA  1350
     TE_D   TAS_E
     CAAGAAGGAAGCCCTAAGTGCTCACCCCACGGGCGCTGCCGGCCACCACAGGCGCCATGGTCGCCTACCAGACGAGCTAGGGGTGCGCGT
                     End Ser His Pro Ala Arg Ser Pro Arg His His Gly Arg Tyr Trp Arg Ile Thr Gln Glu Ile Gly Val Arg Leu
                     <-------------------------- tylD ---------------------------

1351 GGGGCCTGGGTTCGCAGCCGGTGACGTCACGCATCCGCGACAGGTCCAGGCGCTGGGCCGGAGGACCGGAGGGCTTGTCCGGGTAGGTGC  1440
     CCCCGGACCCAAGCGTCGGCCACTGCAGTGCGTAGGCGCTGTCCAGGTCCGCGACCCGGCCTCCTGGCCTCCCGAACAGGCCCATCCACG
     Pro Arg Pro Glu Cys Gly Thr Val Asp Arg Met Arg Ser Leu Asp Leu Arg Gln Ala Pro Pro Gly Ser Pro Lys Asp Pro Tyr Thr Arg
```

-continued

```
     <---------------------------------- tylD ----------------------------------

1441 GGATGCCTCCCTTCCCGCCGACGGCCGAGACCACGGTCCTGGCCAGGTCGAGGATGGACACCTCTTCGGGGGAGCCGATGTTCATCACCG 1530
     CCTACGGAGGGAAGGGCGGCTGCCGGCTCTGGTGCCAGGACCGGTCCAGCTCCTACCTGTGGAGAAGCCCCCTCGGCTACAAGTAGTGGC
     Ile Gly Gly Lys Gly GlyValAla Ser ValVal ThrArgAla LeuAsp Leu Ile Ser Val Glu Glu Pro Ser Gly Ile Asn MetVal Pro

     <---------------------------------- tylD ----------------------------------

1531 GGTACTTGTCCGCCTCGACCATGCGGAGGGTGGCGTTCACCAGGTCCTCCACATGGATGAAGGAACGGGTCTGACGGCCGTCCCCCCAGA 1620
     CCATGAACAGGCGGAGCTGGTACGCCTCCCACCGCAAGTGGTCCAGGAGGTGTACCTACTTCCTTGCCCAGACTGCCGGCAGGGGGGTCT
                                          TS_E
     Tyr LysAsp Ala GluVal MetArg Leu ThrAlaAsnVal LeuAsp Glu Val His Ile Phe Ser Arg Thr GlnArg Gly Asp Gly Trp Ile

     <---------------------------------- tylD ----------------------------------

1621 TCTCTATCGTCTCGCCCGCCGCGGCCCGGGCGACCATGCTGGGAATGACCCGGGTGCGGGTTCCGCCGTTCCCGTCCCGGGGCCCGTAGA 1710
     AGAGATAGCAGAGCGGGCGGCGCCGGGCCCGCTGGTACGACCCTTACTGGGCCCACGCCCAAGGCGGCAAGGGCAGGGCCCCGGGCATCT
     TS_E
     Glu Ile Thr Glu GlyAlaAla AlaArg AlaVal Met Ser Pro Ile Val Arg ThrArg Thr Gly GlyAsn GlyAspArg Pro Gly Tyr Val

     <---------------------------------- tylD ----------------------------------

1711 CGTTTCCCGGCCGGACCCGGAAGATCCGGCTGCCGAACTCGGCGCCGTGCAGTTCGGCCATGATCGTCGAGAAGATCTTCGACAGGACGT 1800
                                                                  S_D   TAS_D        TAS_D
     GCAAAGGGCCGGCCTGGGCCTTCTAGGCCGACGGCTTGAGCCGCGGCACGTCAAGCCGGTACTAGCAGCTCTTCTAGAAGCTGTCCTGCA
     Asn Gly ProArgValArg Phe Ile Arg Ser Gly Phe Glu Ala Gly His Leu GluAla Met Ile Thr Ser Phe Ile Lys Ser LeuVal Tyr

     <---------------------------------- tylD ----------------------------------

1801 AGCCGTTGCCGGCGTGCGGCACATAACGGCGGATCTCCTCGTCCTCCCGGGCCGGGGAGTCCCGCGGGGCGCAGTACACCTCGGTGGAGC 1890
     TCGGCAACGGCCGCACGCCGTGTATTGCCGCCTAGAGGAGCAGGAGGGCCCGGCCCCTCAGGGCGCCCCGCGTCATGTGGAGCCACCTCG
                         S_D                                                     S_D
     Gly Asn Gly Ala His Pro Val Tyr Arg Arg Ile Glu Glu Asp Glu Arg Ala Pro Ser Asp Arg Pro Ala Cys Tyr Val Glu Thr Ser Ser

     <---------------------------------- tylD ----------------------------------

1891 TGAGGAGGACCACCGCGCCGGCGCCGGTGTCCCGGGCGGTGTTGAGCACATGGGCGGTGCCGCGCACGTTCGCGTCCAGGACGGAGGCGG 1980
                                                                                 TAS_D
     ACTCCTCCTGGTGGCGCGGCCGCGGCCACAGGGCCCGCCACAACTCGTGTACCCGCCACGGCGCGTGCAAGCGCAGGTCCTGCCTCCGCC
                S_D                          S_D              S_D
     Leu Leu Val Val Ala Gly Ala Gly Thr Asp Arg Ala Thr Asn Leu Val His Ala Thr Gly Arg Val

     <------------------------------ tylD ------------------------------

1981 AATGGTCGCGCTTGTACTGGGCGTTGCCGTCCAGCCCCGCGTAGTGGATGACGACGTCGGCCCCGGGCGCCCACTCCTGGAAGGCCCTGC 2070
     TTACCAGCGCGAACATGACCCGCAACGGCAGGTCGGGGCGCATCACCTACTGCTGCAGCCGGGGCCCGCGGGTGAGGACCTTCCGGGACG
```

-continued

```
2071 GGGTGGCGGCCTCGTCGCACAGATCGGCCCGTACCAGGCACGACCGGCCGGCCGCCGGCGCCGCCGGTTCCGCTCCGGCCGCCGGGCGGG 2160
     CCCACCGCCGGAGCAGCGTGTCTAGCCGGGCATGGTCCGTGCTGGCCGGCCGGCGGCCGCGGCGGCCAAGGCGAGGCCGGCGGCCCGCCC

2161 CGCTCCCGGTGGAGGCCGACGACCCGGGCGCCGAGGGCGGCGAAGCCGCTCCGCGTAGTGGGAGCCGATGAAGCCCAGGGCGCCGGTGAC 2250
     GCGAGGGCCACCTCCGGCTGCTGGGCCCGCGGCTCCCGCCGCTTCGGCGAGGCGCATCACCCTCGGCTACTTCGGGTCCCGCGGCCACTG

2251 AACCACCGTCCGCCCGGCCCAGTCGCCCGCGGCCCTCATGCGTCGCGCCCGGTGGGCGGAGCGGCGGCCCCGGCCCCGGCTCCGGTCCCG 2340
     TTGGTGGCAGGCGGGCCGGGTCAGCGGGCGCCGGGAGTACGCAGCGCGGGCCACCCGCCTCGCCGCCGGGGCCGGGGCCGAGGCCAGGGC
                                        End Ala Asp Arg Gly Thr Pro Pro Ala Ala Ala Gly Ala Gly Ala Gly Thr Gly
                                        <---------------- tylH ----------------

2341 TCACCGGACAGCAGCACGGCACGGGCCGGGCAGAGGTCCTCCGCCTCCCGTACCTCCTCCCATACCGCGGGCGGGGGCGTCCGGTCCAGC 2430
     AGTGGCCTGTCGTGCTGCCGTGCCCGGCCCGTCTCCAGGAGGCGGAGGGCATGGAGGAGGGTATGGCGCCCGCCCCCGCAGGCCAGGTCG
     Asp Gly Ser Leu Leu Val Ala Arg Ala Pro Cys Leu Asp Glu Ala Glu Arg Val Glu Glu Trp Val Ala Pro Pro Pro Thr Arg Asp Leu
     <---------------- tylH ----------------

2431 ACCCCTCCCACGCCGTCCTCGTCCTGCCGGAAGACGGTGGGCGCCGCCCGCTCGCACTGTCCCGCTCCGACGCAGCGGCCGGTGTCGATC 2520
     TGGGGAGGGTGCGGCAGGAGCAGGACGGCCTTCTGCCACCCGCGGCGGGCGAGCGTGACAGGGCGAGGCTGCGTCGCCGGCCACAGCTAG
     Val Gly Gly Val Gly Asp Glu Asp Gln Arg Phe Val Thr Pro Ala Ala Arg Glu Cys Gln Gly Ala Gly Val Cys Arg Gly Thr Asp Ile
     <---------------- tylH ----------------

2521 CTCACGCGCATCCGTGACTGCTCCTTGTCGTCCTCGCGGCCTGCCGTCCACCAGGCGACGGGCAGCTCGTACACCCCGAAGACCGCGGAG 2610
     GAGTGCGCGTAGGCACTGACGAGGAACAGCAGGAGCGCCGGACGGCAGGTGGTCCGCTGCCCGTCGAGCATGTGGGGCTTCTGGCGCCTC
     Arg Val Arg Met Arg Ser Gln Glu Lys Asp Asp Glu Arg Gly Ala Thr Trp Trp Ala Val Pro Leu Glu Tyr Val Gly Phe Val Ala Ser
     <---------------- tylH ----------------

2611 TCGCTCTTGAGCCGCAGCCCGGCGACGTCCGTGGTCGGCCGCAGTGCGGGCAGCCTCTCCAGCACGGCGCCGAGGGCCACTTCCAGTTCC 2700
     AGCGAGAACTCGGCGTCGGGCCGCTGCAGGCACCAGCCGGCGTCACGCCCGTCGGAGAGGTCGTGCCGCGGCTCCCGGTGAAGGTCAAGG
     Asp Ser Lys Leu Arg Leu Gly Ala Val Asp Thr Thr Pro Arg Leu Ala Pro Leu Arg Glu Leu Val Ala Gly Leu Ala Val Glu Leu Glu
     <---------------- tylH ----------------

2701 ATCCGGGCGAGGTTCTGTCCCAGGCACTGGTGGGGTCCGTAGCCGAAGGCGACATGCCGCCTCGCGGACCGGTGGATGTCGAAGGCCTCC 2790
     TAGGCCCGCTCCAAGACAGGGTCCGTGACCACCCCAGGCATCGGCTTCCGCTGTACGGCGGAGCGCCTGGCCACCTACAGCTTCCGGAGG
     Met Arg Ala Leu Asn Gln Gly Leu Cys Gln His Pro Gly Tyr Gly Phe Ala Val His Arg Arg Ala Ser Arg His Ile Asp Phe Ala Glu
     <---------------- tylH ----------------

2791 GGTTCGGAGAAGACGGCCTCGTCCCGGTTGGCCGCGGCCAGCAGGAAGACCAGGCCGTCGCCGGCGCGGATGGTGTGGCCGTCGATCTCG 2880
     CCAAGCCTCTTCTGCCGGAGCAGGGCCAACCGGCGCCGGTCGTCCTTCTGGTCCGGCAGCGGCCGCGCCTACCACACCGGCAGCTAGAGC
     Pro Glu Ser Phe Val Ala Glu Asp Arg Asn Ala Ala Ala Leu Leu Phe Val Leu Gly Asp Gly Ala Arg Ile Thr His Gly Asp Ile Glu
     <---------------- tylH ----------------
```

-continued

```
2881 ATGTCCGCGGTGGCCGAGCGGCGCAGCCCGTCGGCGATCGACAGATAGCGCAGCAGTTCGTCCACCGCGCCCGGCAACAGGCCGGGATTC 2970
     TACAGGCGCCACCGGCTCGCCGCGTCGGGCAGCCGCTAGCTGTCTATCGCGTCGTCAAGCAGGTGGCGCGGGCCGTTGTCCGGCCCTAAG
     Ile Asp Ala Thr Ala Ser Arg Arg Leu Gly Asp Ala Ile Ser Leu Tyr Arg Leu Leu Glu Asp Val Ala Gly Pro Leu Leu Gly Pro Asn
     <---------------------------------------- tylH ----------------------------------------

2971 ACGGTGAGTTCGCGCCAGGCCGTGGGGTGCTGTAGCAGAACGAGCACGCTCATCGTGACCATGCTGGCCGTGGTCTCGTGCCCGGCGGCC 3060
     TGCCACTCAAGCGCGGTCCGGCACCCCACGACATCGTCTTGCTCGTGCGAGTAGCACTGGTACGACCGGCACCAGAGCACGGGCCGCCGG
     Val Thr Leu Glu Arg Trp Ala Thr Pro His Gln Leu Leu Val Leu Val Ser Met Thr Val Met Ser Ala Thr Thr Glu His Gly Ala Ala
     <---------------------------------------- tylH ----------------------------------------

3061 AGCAGGAGCACCGCGTTGTCCAGGACGTCGGCGTGCGACAGCCCGCCACCGCGGGCCTGCGCCACCATGCTGCCGAGCATCCCGTCGCCG 3150
     TCGTCCTCGTGGCGCAACAGGTCCTGCAGCCGCACGCTGTCGGGCGGTGGCGCCCGGACGCGGTGGTACGACGGCTCGTAGGGCAGCGGC
     Leu Leu Leu Val Ala Asn Asp Leu Val Asp Ala His Ser Leu Gly Gly Gly Arg Ala Gln Ala Val Met Ser Gly Leu Met Gly Asp Gly
     <---------------------------------------- tylH ----------------------------------------

3151 GATTCCCGGCCGGTCTTGCCGCTGATCAGCCGGTCGAGGTAGTCGCGCAGCTCCAGCAGCGCCTCCAGCGCCTCCTCGCCGGCCGCGGGG 3240
     CTAAGGGCCGGCCAGAACGGCGACTAGTCGGCCAGCTCCATCAGCGCGTCGAGGTCGTCGCGGAGGTCGCGGAGGAGCGGCCGGCGCCCC
     Ser Glu Arg Gly Thr Lys Gly Ser Ile Leu Arg Asp Leu Tyr Asp Arg Leu Glu Leu Leu Ala Glu Leu Ala Glu Glu Gly Ala Ala Pro
     <---------------------------------------- tylH ----------------------------------------

3241 CGGGTGGCCTGTTCGGTGCGCTCCTGGAAGTAGTCCCGGTCCTCGTAGGGGATGTCGAGCAGCCGGCAGATCACCTGGGTCGCCATGGGG 3330
     GCCCACCGGACAAGCCACGCGAGGACCTTCATCAGGGCCAGGAGCATCCCCTACAGCTCGTCGGCCGTCTAGTGGACCCAGCGGTACCCC
     Arg Thr Ala Gln Glu Thr Arg Glu Gln Phe Tyr Asp Arg Asp Glu Tyr Pro Ile Asp Leu Leu Arg Cys Ile Val Gln Thr Ala Met Pro
     <---------------------------------------- tylH ----------------------------------------

3331 AGCGCGAAGTCGGCCAGCAGATCCGCCTCGTCGCCGCGGGCGGTGAGGTCATCCAGCAGGCCGGTGACGATCTGTTCGACGGAGGGGCGC 3420
     TCGCGCTTCAGCCGGTCGTCTAGGCGGAGCAGCGGCGCCCGCCACTCCAGTAGGTCGTCCGGCCACTGCTAGACAAGCTGCCTCCCCGCG
     Leu Ala Phe Asp Ala Leu Leu Asp Ala Glu Asp Gly Arg Ala Thr Leu Asp Asp Leu Leu Gly Thr Val Ile Gln Glu Val Ser Pro Arg
     <---------------------------------------- tylH ----------------------------------------

3421 AGCTCCCGCACCCGCCGCAGGCCGAACTCGGGGATGAAGTGGCCGCGGAGCGCTCCGTGGTCGGGCGGGTCCAGTGTCAGCAGCGAACGG 3510
     TCGAGGGCGTGGGCGGCGTCCGGCTTGAGCCCCTACTTCACCGGCGCCTCGCGAGGCACCAGCCCGCCCAGGTCACAGTCGTCGCTTGCC
     Leu Glu Arg Val Arg Arg Leu Gly Phe Glu Pro Ile Phe His Gly Arg Leu Ala Gly His Asp Pro Pro Asp Leu Thr Leu Leu Ser Arg
     <---------------------------------------- tylH ----------------------------------------

3511 GACGCCTCGGCCTCACCGTCGGAGGGTGAGAGCCGCGGGAGCTTCGCGGGATGGATGCTGACCCGGGGGTCGGCCAGCAGCGCCCGGACG 3600
     CTGCGGAGCCGGAGTGGCAGCCTCCCACTCTCGGCGCCCTCGAAGCGCCCTACCTACGACTGGGCCCCCAGCCGGTCGTCGCGGGCCTGC
     Ser Ala Glu Ala Glu Gly Asp Ser Pro Ser Leu Arg Pro Leu Lys Ala Pro His Ile Ser Val Arg Pro Asp Ala Leu Leu Ala Arg Val
     <---------------------------------------- tylH ----------------------------------------

3601 TGATCCTGGCGGGAGATCAGCCAGACCGGCGCCCCGTCCCACAGCTCGGCCCGGGCGATCGGCTCCTCCGCCCGGAGGGCGGCGTACTGC 3690
```

-continued

```
     ACTAGGACCGCCCTCTAGTCGGTCTGGCCGCGGGGCAGGGTGTCGAGCCGGGCCCGCTAGCCGAGGAGGCGGGCCTCCCGCCGCATGACG
     His Asp Gln Arg Ser Ile Leu Trp Val Pro Ala Gly Asp Trp Leu Glu Ala Arg Ala Ile Pro Glu Glu Ala Arg Leu Ala Ala Tyr Gln
     <--------------------------------------- tylH ---------------------------------------

3691 TCGGGAGGGCTGAAGGGACAGGTGCGGGCGACCGGCCAGGCGATGCTGCGCCGGCCTGCGGCCTCGTCGGTGTCGTTGGCGCGTGCTGCG 3780
     AGCCCTCCCGACTTCCCTGTCCACGCCCGCTGGCCGGTCCGCTACGACGCGGCCGGACGCCGGAGCAGCCACAGCAACCGCGCACGACGC
     Glu Pro Pro Ser Phe Pro Cys Thr Arg Ala Val Pro Trp Ala Ile Ser Arg Arg Gly Ala Ala Glu Asp Thr Asp Asn Ala Arg Ala Ala
     <--------------------------------------- tylH ---------------------------------------

3781 GGCAACAGAATCCCCTTTTGTGACGGGCGGGCGTCCCCGGACGAGGACACGACTCGCTGCGGCCTCAACGAAAACACCGTGTCCGGTGCC 3870
     CCGTTGTCTTAGGGGAAAACACTGCCCGCCCGCAGGGGCCTGCTCCTGTGCTGAGCGACGCCGGAGTTGCTTTTGTGGCACAGGCCACGG
                                                    S_H                                 S_H
     Pro Leu Leu Ile Gly Lys Gln Ser Pro Arg Ala Asp Gly Ser Ser Ser Val Val Arg Gln Pro Arg Leu Ser Phe Val Thr Asp Pro Ala
     <--------------------------------------- tylH ---------------------------------------

                                                                                                  TS_F
3871 CAGGCCACGAACGGTGACCGGTCTGTGTCAGGTCGCCCGTGGTGACGGGCTCCGGGGCGGCGGCGCGGGCGGCCGACCTTGACATACCCG 3960
     GTCCGGTGCTTGCCACTGGCCAGACACAGTCCAGCGGGCACCACTGCCCGAGGCCCCGCCGCCGCGCCCGCCGGCTGGAACTGTATGGGC
          S_H
     Trp Ala Val Phe Pro Ser Arg Asp Thr Asp Pro Arg Gly His His Arg Ala Gly Pro Arg Arg Arg Pro Arg Gly Val Lys Val Tyr Gly
     <--------------------------------------- tylH ---------------------------------------

                                                         TS_F
3961 CGGCCGGGCTCCTCGTTCCGGCGCGGCCCGCGCCGATAGCGTCCGTCCTCACCGGCTCCGGCGTCCGCGTCCCCGCCGGGACGTGCCACC 4050
                                                                                                  TS_H
     GCCGGCCCGAGGAGCAAGGCCGCGCCGGGCGCGGCTATCGCAGGCAGGAGTGGCCGAGGCCGCAGGCGCAGGGGCGGCCCTGCACGGTGG
                                                                                                   S_H
     Arg Gly Pro Glu Glu Asn Arg Arg Pro Gly Arg Arg Tyr Arg Gly Asp Glu Gly Ala Gly Ala Asp Ala Asp Gly Gly Pro Arg Ala Val
     <--------------------------------------- tylH ---------------------------------------

                                         TAS_F
4051 TCTCCCGACCCCGCGAGCCGATCGACCCGCTACTGGAGGACCCGTGGCACCTTCCCCGGACCACGCCCGCGATCTCTACATCGAGCTGCT 4140
     TAS_H  TS_H                                  S_F
     AGAGGGCTGGGGCGCTCGGCTAGCTGGGCGATGACCTCCTGGGCACCGTGGAAGGGGCCTGGTGCGGGCGCTAGAGATGTAGCTCGACGA
                                                  Val Ala Pro Ser Pro Asp His Ala Arg Asp Leu Tyr Ile Glu Leu Leu
                                                  ------------ tylF ------------>

4141 GAAGAAGGTCGTCTCGAACGTCATCTACGAGGACCCCACCCATGTGGCGGGGATGATCACCGACGCGTCGTTCGACCGGACGTCCCGTGA 4230
```

-continued

```
                                                                          TSH
     CTTCTTCCAGCAGAGCTTGCAGTAGATGCTCCTGGGGTGGGTACACCGCCCCTACTAGTGGCTGCGCAGCAAGCTGGCCTGCAGGGCACT
     Lys Lys Val Val Ser Asn Val Ile Tyr Glu Asp Pro Thr His Val Ala Gly Met Ile Thr Asp Ala Ser Phe Asp Arg Thr Ser Arg Glu
     ----------------------------------------tylF---------------------------------------->

4231 GAGCGGCGAGGACTACCCCACGGTCGCCCACACGATGATCGGCCTCAAGCGTCTGGACAATCTCCACCGGTGCCTCGCGGACGTCGTGGA 4320
     CTCGCCGCTCCTGATGGGGTGCCAGCGGGTGTGCTACTAGCCGGAGTTCGCAGACCTGTTAGAGGTGGCCACGGAGCGCCTGCAGCACCT
     Ser Gly Glu Asp Tyr Pro Thr Val Ala His Thr Met Ile Gly Leu Lys Arg Leu Asp Asn Leu His Arg Cys Leu Ala Asp Val Val Glu
     ----------------------------------------tylF---------------------------------------->

4321 GGACGGCGTCCCCGGTGACTTCATCGAGACCGGGGTGTGCCGCGCGCCGTGCATCTTCGCCCGCGGACTGCTGAACGCGTACGGCCAGGC 4410
     CCTGCCGCAGGGGCCACTGAAGTAGCTCTGGCCCCACACGGCGCGCGGCACGTAGAAGCGGGCGCCTGACGACTTGCGCATGCCGGTCCG
     Asp Gly Val Pro Gly Asp Phe Ile Glu Thr Gly Val Cys Arg Ala Pro Cys Ile Phe Ala Arg Gly Leu Leu Asn Ala Tyr Gly Gln Ala
     ----------------------------------------tylF---------------------------------------->

4411 CGACCGCACCGTCTGGGTCGCCGACTCCTTCCAGGGCTTTCCCGAGCTGACCGGGTCCGACCACCCGCTGGACGTCGAGATCGACCTCCA 4500
     GCTGGCGTGGCAGACCCAGCGGCTGAGGAAGGTCCCGAAAGGGCTCGACTGGCCCAGGCTGGTGGGCGACCTGCAGCTCTAGCTGGAGGT
     Asp Arg Thr Val Trp Val Ala Asp Ser Phe Gln Gly Phe Pro Glu Leu Thr Gly Ser Asp His Pro Leu Asp Val Glu Ile Asp Leu His
     ----------------------------------------tylF---------------------------------------->

4501 CCAGTACAACGAGGCCGTGGACCTGCCCACCAGCGAGGAGACCGTGCGGGAGAACTTCGCCCGGTACGGGCTGCTCGACGACAACGTCCG 4590
     GGTCATGTTGCTCCGGCACCTGGACGGGTGGTCGCTCCTCTGGCACGCCCTCTTGAAGCGGGCCATGCCCGACGAGCTGCTGTTGCAGGC
     Gln Tyr Asn Glu Ala Val Asp Leu Pro Thr Ser Glu Glu Thr Val Arg Glu Asn Phe Ala Arg Tyr Gly Leu Leu Asp Asp Asn Val Arg
     ----------------------------------------tylF---------------------------------------->

4591 TTTCCTGGCGGGGTGGTTCAAGGACACCATGCCGGCTGCGCCCGTGAAGCAGCTCGCGGTGATGCGCCTGGACGGCGACTCCTACGGCGC 4680
     AAAGGACCGCCCCACCAAGTTCCTGTGGTACGGCCGACGCGGGCACTTCGTCGAGCGCCACTACGCGGACCTGCCGCTGAGGATGCCGCG
     Phe Leu Ala Gly Trp Phe Lys Asp Thr Met Pro Ala Ala Pro Val Lys Gln Leu Ala Val Met Arg Leu Asp Gly Asp Ser Tyr Gly Ala
     ----------------------------------------tylF---------------------------------------->

4681 CACCATGGATGTGCTCGACAGCCTGTACGAGCGGCTGTCGCCGGGCGGTTACGTCATCGTCGACGACTACTGCATCCCGGCCTGCCGCGA 4770
     GTGGTACCTACACGAGCTGTCGGACATGCTCGCCGACAGCGGCCCGCCAATGCAGTAGCAGCTGCTGATGACGTAGGGCCGGACGGCGCT
     Thr Met Asp Val Leu Asp Ser Leu Tyr Glu Arg Leu Ser Pro Gly Gly Tyr Val Ile Val Asp Asp Tyr Cys Ile Pro Ala Cys Arg Glu
     ----------------------------------------tylF---------------------------------------->

                                                                ******         ******
4771 GCGGTGCACGACTTCCGCGACCGGCTCGGCATCCGCGACACGATCCACCGGATCGACCGCCAGGGCGCTATTGGCGGCACAGCGGCTGAG 4860
     CGCCACGTGCTGAAGGCGCTGGCCGAGCCGTAGGCGCTGTGCTAGGTGGCCTAGCTGGCGGTCCCGCGATAACCGCCGTGTCGCCGACTC
                                                                ******         ******
     Arg Cys Thr Thr Ser Ala Thr Gly Ser Ala Ser Ala Thr Arg Ser Thr Gly Ser Thr Ala Arg Ala Leu Leu Ala Ala Gln Arg Leu Ser
     ----------------------------------------tylF---------------------------------------->
```

-continued

```
4861 TCGTTCCGCCCGAGAGCCCGACGAGAGCAGGAGATATGCGAGACACGACGCGCCCGCTCGGCATTGAGGGAGCGTGGGTGATCCAGCCGG 4950
     AGCAAGGCGGGCTCTCGGGCTGCTCTCGTCCTCTATACGCTCTGTGCTGCGCGGGCGAGCCGTAACTCCCTCGCACCCACTAGGTCGGCC
     Arg Ser Ala Arg Glu Pro Asp Glu Ser Arg Arg Tyr Ala Arg His Asp Ala Pro Ala Arg His End
     ---------------------------------tylF-------------------------------->

                                                                   ******      ******
4951 AGATCCATCCGGACCGGCGCGGCGAGTTCCACGCGTGGTTCCAGAGCCAGCCGAGTTCCGGCGGCTGACCGGTCACTCCTTCTCCGTGCC 5040
     TCTAGGTAGGCCTGGCCGCGCCGCTCAAGGTGCGCACCAAGGTCTCGGTCGGCTCAAGGCCGCCGACTGGCCAGTGAGGAAGAGGCACGG
                                                                   ******      ******

5041 GCAGGTCAATATCGCGTGTCCCGGAAAGGCGCGCTCGCGGCATCCACTTCTCCGAGGTGCCACCGGGCCAGGCCAAGTACAGCGCGTGTG 5130
     CGTCCAGTTATAGCGCACAGGGCCTTTCCGCGCGAGCGCCGTAGGTGAAGAGGCTCCACGGTGGCCCGGTCCGGTTCATGTCGCGCACAC
          End Tyr Arg Thr Asp Arg Phe Pro Ala Ser Ala Ala Asp Val Glu Gly Leu His Trp Arg Ala Leu Gly Leu Val Ala Arg Thr
     <--------------------------------tylJ----------------------------------

5131 TGCAGGGCGCCGGTGTCGAGGTCGTCGTCGACATCCGGCGGGCTCCCCCACCTACGGGCAGTGGCGGGCGGTGCGTCGACGAGTACAACC 5220
     ACGTCCCGCGGCCACAGCTCCAGCAGCAGCTGTAGGCCGCCCGAGGGGGTGGATGCCCGTCACCGCCCGCCACGCAGCTGCTCATGTTGG
     His Leu Ala Gly Thr Asp Leu Asp Asp Asp Val Asp Pro Pro Ser Gly Trp Arg Arg Ala Thr Ala Pro Pro Ala Asp Val Leu Val Val
     <--------------------------------tylJ----------------------------------

5221 GGACCGCCGTCTATGTGCCCGCAGGGCTGGGCCGGGCCTTCGTCGCGCTCACCGACCGCACCACGCTGGTCTATCTCTGCTCCAGCGAAT 5310
     CCTGGCGGCAGATACACGGGCGTCCCGACCCGGCCCGGAAGCAGCGCGAGTGGCTGGCGTGGTGCGACCAGATAGAGACGAGGTCGCTTA
     Pro Gly Gly Asp Ile His Gly Cys Pro Gln Ala Pro Gly Glu Asp Arg Glu Gly Val Ala Gly Arg Gln Asp Ile Glu Ala Gly Ala Phe
     <--------------------------------tylJ----------------------------------

5311 ACGCGGCCCGGCGGGAGCACGCCGTCAATCCCCTGGACCCCGATCTCGCGATCGCCTGGCCCGAGGACGTCGAGCTGCTGCTCTCGGAGC 5400
     TGCGCCGGGCCGCCCTCGTGCGGCAGTTAGGGGACCTGGGGCTAGAGCGCTAGCGGACCGGGCTCCTGCAGCTCGACGACGAGAGCCTCG
     Val Arg Gly Pro Pro Leu Val Gly Asp Ile Gly Gln Val Gly Ile Glu Arg Asp Gly Pro Gly Leu Val Asp Leu Gln Gln Glu Arg Leu
     <--------------------------------tylJ----------------------------------

5401 GGGACACCCGGGCGCCCACGCTGGCCGAGGCGGCGCGGCGCGGGATTCTGCCCTCCTACCAGGAGTACCGGGAGCACCACGGTCTGCCGC 5490
     CCCTGTGGGCCCGCGGGTGCGACCGGCTCCGCCGCGCCGCGCCCTAAGACGGGAGGATGGTCCTCATGGCCCTCGTGGTGCCAGACGGCG
     Pro Val Gly Pro Arg Gly Arg Gln Gly Leu Arg Arg Pro Ala Pro Asn Gln Gly Gly Val Leu Leu Val Pro Leu Val Val Thr Gln Arg
     <--------------------------------tylJ----------------------------------

        **************    **************
5491 CGGAGCACGCCCGGCGGTAGGCACCGCCGGGCGAGCGGGCCCGGCCGCTCGTCCTCCGGCCGCTCCGGCGGGGCCGTGGCGCCGAGCGTG 5580
     GCCTCGTGCGGGCCGCCATCCGTGGCGGCCCGCTCGCCCGGGCCGGCGAGCAGGAGGCCGGCGAGGCCGCCCCGGCACCGCGGCTCGCAC
        **************    **************
     Arg Leu Val Gly Pro Pro Leu Cys Arg Arg Ala Leu Pro Gly Pro Arg Glu Asp Glu Pro Arg Glu Pro Pro Ala Thr Ala Gly Leu Thr
     <--------------------------------tylJ----------------------------------

5581 ACGGCCCGGGGGATGTCGGGCTCCCGCCCGGCCGCCGTCCTCCGCCCCGCGGGGACCTGCCCTCGGCCTCCCGCGGCACGGAGCCCGTA 5670
```

-continued

```
                                                                                     SJ
TGCCGGGCCCCCTACAGCCCGAGGGCGGGCCGGCGGCAGGAGGCGGGGCGCCCCCTGGACGGGAGCCGGAGGGCGCCGTGCCTCGGGCAT
Val Ala Arg Pro Ile  Asp Pro Glu Arg Gly Ala Ala Thr Arg Arg Gly Ala Pro Ser Arg Gly Glu Ala Glu Arg Pro Val

<------------------------------------- tylJ -----------------------------------------

5671 CGCGGACAGGAGGGTGTCGACGATCTGGTCGAAGCGCGTCTCGTGGGCGGCGTTCGCCAGGGGGATGCCGCCGAGGAACTCCCCGGGCAG 5760
       TSJ                                  TSJ
     GCGCCTGTCCTCCCACAGCTGCTAGACCAGCTTCGCGCAGAGCACCCGCCGCAAGCGGTCCCCCTACGGCGGCTCCTTGAGGGGCCCGTC

5761 ATCGAAGGCCTCGACGAGCGTCATCATGTGCGGGGCGAGGCCCGCGATCACCTCGTCCACG 5821
     TAGCTTCCGGAGCTGCTCGCAGTAGTACACGCCCCGCTCCGGGCGCTAGTGGAGCAGGTGC
```

wherein A is a deoxyadenyl residue; G is a deoxyguanyl residue; C is a deoxycytidyl residue; T is a thymidyl residue; ALA is alanine, RAG is arginine, ASN is asparagine, ASP is aspartic acid, CYS is cysteine, GLN is glutamine, GLU is glutamic acid, GLY is glycine, HIS is histidine, ILE is isoleucine, LEU is leucine, LYS is lysine, MET is methionine, PHE is phenylalanine, PRO is proline, SER is serine, THR is theonine, TRP is tryptophan, TYR is tyrosine, and VAL is valine.

The arrows on the DNA and amino acid sequence map data above indicate the direction of transcription for each of the designated genes. In particular, one skilled in the art will appreciate that the tylE, tylD, tylH and tylJ gene products are encoded on one DNA strand. The tylF gene, however, is transcribed from the complementary strand. Initiation of translation in streptomycetes occurs at GTG codons as well as ATG codons. In the present case, initiation of translation of the tylH, tylF and tylJ genes most likely occurs at a GTG codon. The tylE gene probably starts at an ATG codon whereas the tylD gene may initiate at either an ATG or GTG.

Furthermore, transcription mapping shows that the transcript for the tylE gene overlaps the transcript of the tylD and tylH genes. Also, the tylH transcript overlaps the transcript of the tylF gene. Asterisks on the map indicate inverted repeat sequence which may be able to form stem-loop structures.

Also noted on this map are possible translational activating sequences for several of the genes. Also, the transcription termination site for the tylD gene appears to be located only one base pair from the gene appears to be located only one base pair from the tylE translation start codon.

*Streptomyces fradiae* strains can be cultured in a number of ways using any of several different media. Carbohydrate sources that are preferred in a culture medium include, for example, molasses, glucose, dextran, and glycerol, an nitrogen sources include, for example, soy flour, amino acid mixtures, and peptones. Nutrient inorganic salts are also incorporated into the medium and include the customary salts capable of yielding sodium, potassium, ammonium, calcium, phosphate, chloride, sulfate, and like ions. As is necessary for the growth and development of other microorganisms, essential trace elements are also added. Such trace elements are commonly supplied as impurities incidental to the addition of other constituents of the medium. *S. fradiae* strains are grown under aerobic culture conditions over a relative wide pH range of about 6 to 8 at temperatures ranging from about 25° to 37° C.

The following examples further illustrate and describe the invention disclosed herein. The invention is not limited in scope by reason of any of the following Examples; sources of reagents are provided merely for convenience and in no way limit the invention. Both an explanation of and the actual procedures for constructing the invention are described where appropriate.

EXAMPLE 1

Isolation of Plasmid pHJL280

A. Culture of *E. coli* K12 HB101/pHJL280

Lyophils of *E. coli* K12 HB101/pHJL280 can be B-18043. The lyophilized cells are streaked onto L-agar plates (L agar contains 10 g of Bacto Tryptone, 5 g of Bacto Yeast Extract, 10 g of NaCl, 2 g of glucose, and 15 g of agar per liter) containing 50 μg/ml ampicillin to obtain a single-colony isolate of *E. coli* K12 HB101/pHJL280. One such colony was used to inoculate 100 ml of L broth (L broth is L agar without the agar), which was then incubated aerobically at 37° C. overnight (about 16 hours). The following morning, the cells were harvested by centrifugation at 10,000×g for 10 minutes. The ~1 g of cells obtained by this procedure are used to prepare plasmid pHJL280 DNA in substantial accordance with the procedure described below.

B. Plasmid Isolation

The cell pellet obtained in Example 1A was resuspended in 10 ml of a solution composed of 25% sucrose and 50 mM Tris-HCl at a pH=8.0. About 1 ml of a 10 mg/ml solution of lysozyme in 50 mM Tris-HCl at a pH=8.0 was incubated on ice for 5 minutes. About 4 ml of 0.25M EDTA, pH=8.0, were then added to the cell suspension, and incubation on ice was continued for another 5 minutes. About 16 ml of lysis solution (lysis solution contains 0.4% deoxycholate; 1% Brij58 (Sigma Chemical Co., P.O. Box 14508, St. Louis, Mo. 63178); 0.05M Tris-HCl, pH=8.0; and 0.0625M EDTA) were added to the lysozyme-treated cells, and the resulting mixture was incubated at 37° C. for 15 minutes.

The cell lysate was cleared by centrifugation at 48,000×g for 25 minutes. The supernatant was decanted into a separate tube, to which was added 0.1 volume of 3.0M NaOAc at a pH=8.0 and 0.64 volume of isopropyl alcohol. The DNA precipitate was collected by centrifugation at 20,000×g for 10 minutes and then redissolved in 0.1 volume of TE buffer (10 mM Tris-HCl, pH=7.8, and 1 mM EDTA). The solution of DNA was incubated at 65° C. for 30 minutes and then purified by equilibrium-density-gradient ultracentrifugation in CsCl and propidium diiodide. The plasmid pHJL280 DNA obtained by this procedure was dissolved in TE buffer at a concentration of about 1 μg/μl. A restriction site map of plasmid pHJL280 is presented in FIG. 2 of the accompanying drawings.

EXAMPLE 2

Isolation of Plasmids pHJL284, pHJL309, pHJL311, and pHJL315

Lyophils of the *E. coli* strains harboring plasmids pHJL284, pHJL309, pHJL311, and pHJL315 can be listed in Table X. The desired plasmids are each obtained and purified from the lyophilized cells in substantial accordance with the teaching of Example 1. Restriction site maps of the plasmids are presented in FIGS. 2–6 of the accompanying drawings.

EXAMPLE 3

Construction of *Streptomyces fradiae* GS28/pHJL280

A culture of *Streptomyces fradiae* GS 28 was inoculated into 20 ml of trypticase-soya broth (TSB) and incubated in a water-bath incubator at 29° C. at 260 rpm overnight (about 16 hours). The culture was homogenized using a homogenizing vessel (Thomas Scientific, Swedesboro, N.J.) and a T-Line laboratory stirrer and then fragmented using a Sonifier Cell Disruptor (Heat Systems Ultrasonics, Inc.) for 7 seconds at 76 Watts. Four ml of the homogenized, fragmented culture were inoculated into 20 ml of TSB (BBL) containing 0.3% weight by volume glycine, and the culture was again incubated overnight at 29° C. The following morning, the culture was homogenized and recultured as described above. After this third overnight incubation, the culture was homogenized, collected, and then washed twice with P media (P media was prepared by adding 103 g of sucrose to 0.25 g of $K_2SO_4$ and 2.03 g of $MgCl_2$-$6H_2O$ and then adding deionized water to a final volume of 700 ml. The mixture was then sterilized, and to each 70 ml of solution, about 10 ml each of 0.05 g $KH_2PO_4$/100 ml of deionized water; 2.78 g $CaCl_2$/100 ml of deionized water; and 0.25M TES (2-([tris-(hydroxymethyl)methyl]amino)ethanesulfonic acid)) at a pH=7.2 were added to form the desired P media.

The cell pellet was resuspended in 15 ml of P media containing 1 mg/ml lysozyme (Calbiochem, La Jolla, Calif.

92037) and then incubated at room temperature for about one-and-one-half hours to form protoplasts. The protoplasts were gently collected by centrifugation, washed twice with P media, resuspended in 2 ml of P media, and incubated on ice until use. About 1 μg of plasmid pHJL280 DNA was added to about 50 μl of 2 mg/ml heparin sulfate (Sigma) and incubated on ice for about 10 minutes. Much less plasmid DAN, about 5–100 nanograms, can be used to transform *Streptomyces fradiae* if prepared from a *S. fradiae* host. The procedure for isolating Streptomyces plasmid DNA is described in Hopwood et al., 1985, *Genetic Manipulation* of Streptomyces: *A Laboratory Manual* (John Innes foundation, Norwich, England). The DNA/heparin solution was first added to about 200 μl of protoplasts, and about 0.9 ml of a solution composed of 55% PEG 1000 (Sigma) in P medium was then added to the DNA/protoplast mixture, and the resulting mixture was gently mixed at room temperature.

The mixture was plated in varying aliquots onto R2 plates using 4 ml of soft-R2-agar overlays. R2 plates contain 30 ml of R2 media and have been dried at 37° C. for about 4 days. R2 media is prepared by adding 103 g sucrose, 0.25 g $K_2SO_4$, 2 ml of trace element solution, 10.12 g $MgCl_2$-$6H_2O$, 10.0 g of glucose, 2.0 g of L-asparagine, 0.1 g of Casamino acids, and 22 g of agar to 700 ml of water; sterilizing the resulting solution; and finally, adding 100 ml of each of the following solutions: 0.05 g $KH_2PO_4$/100 ml of deionized water; 2.22 g $CaCl_2$/100 ml of deionized water; and 0.25M TES, pH=7.2. The pH of the final solution is adjusted to equal 7.2. Trace element solution contains 40 mg $ZnCl_2$, 200 mg $FeCl_3$-$6H_2O$, 10 mg $CuCl_2$-$2H_2O$, 10 mg $MnCl_2$-$4H_2O$, 10 mg $Na_2B_4O_7$-$10H_2O$, and 10 mg $(NH_4)_6Mo_7O_{24}$.$4H_2O$ per liter. The soft-R2-agar overlays are prepared by adding 51.5 g of sucrose, 5.06 g $MgCl_2$-$6H_2O$, 1.11 g $CaCl_2$, 50 ml of 0.25M TES at a pH=7.2, and 2.05 g agar to enough deionized water to achieve a final volume of 500 ml. The mixture is steamed to melt the agar, decanted into 4 ml aliquots, and autoclaved prior to use. After the transformed protoplasts had been plated, the plates were incubated at 29° C. for 24 hours, and then, 4 ml of soft-R2 agar containing 25 μl of 50 mg/ml thiostrepton (E. R. Squibb, Princeton, N.J. 08540) were spread over the protoplasts. Incubation of the plates at 29° C. was continued until regeneration was complete, usually a period of about 7–14 days, to select for the desired *S. fradiae* GS28/pHJL280 strain The *Streptomyces fradiae* GS28/pGJL280 strain was cultured and produced macrocin O-methyltransferase and tylosin at levels above that produced in the untransformed *S. fradiae* GS28 strain. Macrocin O-methyltransferase activity was assayed and determined in substantial accordance with the teaching of Yeh et al., 1984, Journal of Chromatography 288:157–165. Comparison of the macrocin O-methyltransferase activities in the transformed, GS28/pHJL280, and parental, GS28, strains showed a 60-to-100-fold increase of enzyme and 14-to-18-fold increase of tylosin production in the transformed strain. Tylosin production was assayed and determined in substantial accordance with the teaching of Baltz and Seno, 1981, Antimicrobial Agents and Chemotherapy 20:214–225; and Kennedy, J. H., 1983, Journal of Chromatography 281:288–292.

EXAMPLE 4

Construction of *Streptomyces fradiae* GS15/pHJL280

The desired strain was constructed in substantial accordance with the teaching of Example 3 except that *Streptomyces fradiae* GS15, rather than *S. fradiae* GS28, was used. The desired strain was cultured for 72 hours and produced macrocin O-methyltransferase and tylosin at levels above that produced in the un-transformed *S. fradiae* GS15 strain, which produces no readily detectable tylosin.

EXAMPLE 5

Construction of *Streptomyces fradiae* GS15, pHJL284

The desired strain was constructed in substantial accordance with the teaching of Example 4 except that plasmid pHJL284, rather than plasmid pHJL280, was used. The desired strain was cultured and produced macrocin O-methyltransferase and tylosin at levels above that produced in the untransformed *S. fradiae* GS15 strain.

EXAMPLE 6

Construction of *Streptomyces fradiae* GS16/pHJL280

The desired strain was constructed in substantial accordance with the teaching of Example 3 except that *Streptomyces fradiae* GS16, rather than *S. fradiae* GS28, was used. The desired strain was cultured and produced the tylE gene product, demethylmacrocin O-methyltransferase, and tylosin at levels above that produced in the untransformed strain. The demethylmacrocin O-methyltransferase activity and tylosin production respectively are assayed and determined in substantial accordance with the above-referenced procedures, except that demethylmacrocin is substituted for macrocin as substrate.

EXAMPLE 7

Construction of *Streptomyces fradiae* GS76/pHJL280

The desired strain was constructed in substantial accordance with the teaching of Example 3 except that *Streptomyces fradiae* GS76, rather than *S. fradiae* GS28, was used. The desired strain was cultured and produced the tylD and tylH gene products and tylosin at levels above that produced in the untransformed strain.

EXAMPLE 8

Construction of *Streptomyces fradiae* GS48/pHJL280

The desired strain was constructed in substantial accordance with the teaching of Example 3 except that *Streptomyces fradiae* GS48, rather than *S. fradiae* GS28, was used. The desired strain was cultured and produced the tylD gene product and tylosin at levels above that produced in the untransformed strain.

EXAMPLE 9

Construction of *Streptomyces fradiae* GS52/pHJL284

The desired strain was constructed in substantial accordance with the teaching of Example 3 except that *Streptomyces fradiae* GS52 and plasmid pHJL284, rather than *S. fradiae* GS28 and plasmid pHJL280, were used. The desired strain was cultured and produced the tylC gene product and tylosin at levels above that produced in the untransformed strain.

EXAMPLE 10

Specific Activity of Rate-Limiting Enzymes and Increased Tylosin Production Using the Present Method The following Tables demonstrate the effectiveness of the present method. All transformants listed in the Tables were obtained in substantial accordance with the procedure of Example 3. The results indicated in Tables XIII and XIV were obtained from strains cultured in fermentation media (Baltz and Seno, 1981, Antimicrobial Agents and Chemotherapy 20:214–225) that also contained 20 μg/ml thiostrepton if the strain being cultured harbored a plasmid. Note that the transformed strains listed in Tables XIII and XIV are low tylosin-producing, or produce amounts of tylosin that are not readily detectable, and were cultured in the presence of selective pressure (thiostrepton) for plasmid maintenance as an autonomously replicating vector.

TABLE XIII

Specific Activity of the tylF Gene Product, Macrocin O-methyltransferase (MOMT)

| | Strain | Transforming Plasmid | MOMT Specific Activity | | | |
|---|---|---|---|---|---|---|
| | | | 2 days[1] | 3 days | 4 days | 6 days |
| Run 1 | GS15 | pHJL210[4] | 0 | 0 | 0 | 0 |
| | GS15 | pHJL280 | 1.14 | 1.93 | NT | NT |
| | C4[2] | None | Not tested (NT) | 0.35 | 0.16 | NT |
| Run 2 | GS15 | pHJL210 | 0 | 0 | 0 | 0 |
| | GS15 | pHJL280 | 4.2 | 3.2 | 2.2 | 1.8 |
| | C4 | None | 0.8 | 1.0 | 0.9 | 0.9 |
| | T1405[3] | None | 0.9 | 1.2 | 1.5 | 1.4 |
| Run 3 | GS15 | pHJL210 | 0 | 0 | NT | NT |
| | GS15 | pHJL289[5] | 0.5 | 0.3 | NT | NT |
| | GS15 | pHJL311 | NT | 0.4 | NT | NT |
| | GS15 | pHJL315 | 0.1 | 0.4 | NT | NT |
| | C4 | None | 0.2 | 0.2 | NT | NT |
| Run 4 | GS28 | None | 0 | 0.01 | 0.03 | NT |
| | GS28 | pHJL210 | 0 | 0 | 0 | NT |
| | GS28 | pHJL280 | 0.8 | 0.7 | 1.0 | NT |
| | GS28 | pHJL284 | 0.9 | 1.2 | 0.9 | NT |
| | C4 | None | 0.2 | 0.6 | 0.5 | NT |

[1]days in fermentation.
[2]the strain from which GS15 and GS28 were derived.
[3]a strain derived from C4.
[4]the cloning vector into which the tylgenes were inserted to obtain plasmids pHJL280 and pHJL284.
[5]pHJL289 is constructed by ligating the ~2.3 kb, tylF-containing, EcoRI-BamHI restriction fragment of pHJL284 into pHJL401.

TABLE XIV

Specific Activity of the tylE Gene Product, Demethylmacrocin O-methyltransferase (DMOMT)

| Strain | Transforming Plasmed | DMBMT Specific Activity | | |
|---|---|---|---|---|
| | | 2 days* | 3 days | 4 days |
| GS16 | pHJL210 | 0 | 0 | 0 |
| GS16 | pHJL280 | 1.8 | 3.7 | 4.0 |
| GS16 | pHJL280 | 3.8 | 1.7 | 3.0 |
| GS16 | pHJL284 | 1.3 | 1.6 | 2.2 |
| C4 | pHJL210 | 0.7 | 1.3 | 1.5 |
| C4 | pHJL210 | 0.2 | 1.1 | 1.9 |
| C4 | None | 0.4 | 1.5 | 1.0 |

The results in Table XV were obtained from transformants of high tylosin-producing strains that were cultured post-transformation to obtain integrants, transformants in which all or part of the plasmid DNA has integrated into the genome of the host cell. Two methods were used to obtain the integrants. In the first method, transformants are passaged onto selective (contains thiostrepton) and nonselective plates and incubated about 16 hours at 29° C. to obtain single colonies. The single colonies on the nonselective plates that were thiostrepton-resistant on the selective plate are repassaged several times in the same manner until a single colony was found to be relatively stable without selection. In the second method for obtaining integrants, the transformants were nonselectively passaged several times by transferring spores from the surface of the plate using a cotton swab. After several passages, the colonies are grown in non-selective, liquid media (TSB), homogenized, fragmented by sonication, diluted, and plated on selective and nonselective media to identify relatively stable integrants.

Other methods of obtaining integrants are apparent to those skilled in the art, and the present method is not limited to a particular method of obtaining integrants.

Relatively stable integrants were used to inoculate vegetative medium (complex vegetative medium contains, per liter, 10 g of corn steep liquor, 5 g of yeast extract, 5 g of soybean grits, 3 g of calcium carbonate, and 4.5 g of crude soybean oil, and the pH is adjusted to 7.8 with NaOH. TSB is also a suitable vegetative media) without thiostrepton (no selective pressure), and the vegetative culture was used to inoculate (10% inoculum) the fermentation medium, which also lacked thiostrepton. Fermentations were run at 260 rpm at 29° C. for seven days. The total macrolide content of the fermentation broth was measured by extraction with methanol:$CHCl_3$, reading the absorbance at 290 nm, and comparing to a standard curve. Tylosin factors were identified by spotting the fermentation broth onto silica-gel-TLC plates and developing the plates with a solvent system of 95:5 ethylacetate:diethylamine. The concentration of individual macrolide components was the total $A_{290}$ times the percentage of each component as determined by HPLC.

TABLE XV

| Strain | % Thiostrepton Resistant | Transforming Plasmed | DMOMT Specific Activity | MOMT Specific Activity | Tylosin* |
|---|---|---|---|---|---|
| C4 | 0 | None | 0.59 | 0.14 | 1 |
| C4 | 9.5 | pHJL280 | Not tested (NT) | NT | 1.10 |
| C4 | 5.9 | pHJL280 | NT | NT | 0.97 |
| T1405 | 0 | None | 1.0 | 0.17 | 1.14 |
| T1405 | 50 | pHJL280 | 0.91 | 0.26 | 1.52 |
| T1405 | 8.7 | pHJL280 | NT | UT | 1.21 |
| T1405 | 11 | pHJL280 | NT | NT | 1.07 |
| T1405 | 6.4 | PHJL280 | NT | UT | 1.21 |
| T1405 | 18 | pHJL280 | 2.5 | 0.43 | 1.60 |
| T1405 | 4.6 | pHJL280 | NT | KT | 0.98 |
| T1405 | 16 | pHJL280 | NT | NT | 1.07 |
| T1405 | 12 | pHJL280 | NT | NT | 1.10 |
| T1405 | 18 | pHJL280 | NT | NT | 1.28 |
| T1405 | 25 | pHJL280 | NT | NT | 1.28 |
| T1405 | 56 | pHJL280 | 0.82 | 0.22 | 1.45 |

*Relative to C4 strain

We claim:

1. The DNA sequence that encodes a gene product selected from the group consisting of the *Streptomyces fradiae* tylC, tylD, tylE, tylF, tylH, tylJ, tylK, tylL, and tylM biosynthetic gene products.

2. The DNA sequence of claim 1 that encodes the tylC gene product.

3. The DNA sequence of claim 1 that encodes the tylD gene product.

4. The DNA sequence of claim 1 that encodes the tylE gene product.

5. The DNA sequence of claim 1 that encodes the tylF gene product.

6. The DNA sequence of claim 1 that encodes the tylH gene product.

7. The DNA sequence of claim 1 that encodes the tylJ gene product.

8. The DNA sequence of claim 1 that encodes the tylK gene product.

9. The DNA sequence of claim 1 that encodes the tylL gene product.

10. The DNA sequence of claim 1 that encodes the tylM gene product.

11. A DNA sequence that encodes the translational-activating sequence of a gene selected from the group consisting of the *Streptomyces fradiae* tylC, tylD, tylE, tylF, tylH, tylJ, tylK, tylL and tylM biosynthetic genes.

12. The DNA sequence of claim 11 which encodes the translational activating sequence of a gene selected from the group consisting of the tylE, tylF, tylD, tylH, and tylJ biosynthetic genes.

13. A plasmid that is selected from the group consisting of plasmids pSKC13, pSKC16, pSFH60, pSFH61, pSFH62, pOJ163, pOJ190, and pHJL289.

14. A DNA sequence that encodes the *Streptomyces fradiae* tylF gene product, said product comprising the amino acid residue sequence:

4110 4130
ValAlaProSerProAspHisAlaArgAspLeuTyrIleGluLeuLeuLys 4150 4170
LysValValSerAsnValIleTyrGluAspProThrHisValAlaGlyMet 4210 4230
IleThrAspAlaSerPheAspArgThrSerArgGluSerGlyGluAspTyr

-continued 4250 4270 4290
ProThrValAlaHisThrMetIleGlyLeuLysArgLeuAspAsnLeuHis 4310 4330 43
ArgCysLeuAlaAspValValGluAspGlyValProGlyAspPheIleGlu 50 4370 4390
ThrGlyValCysArgAlaProCysIlePheAlaArgGlyLeuLeuAsnAla 4410 4430 4450
TyrGlyGlnAlaAspArgThrValTrpValAlaAspSerPheGlnGlyPhe 4470 4490
ProGluLeuThrGlySerAspHisProLeuAspValGluIleAspLeuHis 4510 4530 4550
GlnTyrAsnGluAlaValAspLeuProThrSerGluGluThrValArgGlu 4570 4590
AsnPheAlaArgTyrGlyLeuLeuAspAspAsnValArgPheLeuAlaGly 4610 4630 4650
TrpPheLysAspThrMetProAlaALaProValLysGlnLeuAlaValMet 4670 4690
ArgLeuAspGlyAspSerTyrGlyAlaThrMetAspValLeuAspSerLeu 4710 4730 4750
TyrGluArgLeuSerProGlyGlyTyrValIleValAspAspTyrCysIle 4770 4790 4
ProAlaCysArgGluArgCysThrThrSerAlaThrGlySerAlaSerAla 810 4830 4850
ThrArgSerThrGlySerThrAlaArgAlaLeuLeuAlaAlaGlnArgLeu 4870 4890 491
SerArgSerAlaArgGluProAspGluSerArgArgTyrAlaArgHisAsp 0
AlaProAlaArgHis wherein ALA is alanine, ARG is arginine, ASN is asparagine, ASP is aspartic acid, CYS is cysteine, GLN is glutamine, GLU is glutamic acid, GLY is glycine, HIS is histidine, ILE is isoleucine, LEU is leucine, LYS is lysine, MET is methionine, PHE is phenylalanine, PRO is proline, SER is serine, THR is threonine, TRP is tryptophan, TYR is tyrosine, and VAL is valine.

15. The DNA sequence of claim 14 which is

4100
GTGGCAC
CACCGTG 4110 4130 4150

CTTCCCCGGACCACGCCCGCGATCTCTACATCGAGCTGCTGAAGAAGGTC
GAAGGGGCCTGGTGCGGGCGCTAGAGATGTAGCTCGACGACTTCTTCCAG 4170 4190

GTCTCGAACGTCATCTACGAGGACCCCACCCATGTGGCGGGGATGATCAC
CAGAGCTTGCAGTAGATGCTCCTGGGGTGGGTACACCGCCCCTACTAGTG 4210 4230 4250

CGACGCGTCGTTCGACCGGACGTCCCGTGAGAGCGGCGAGGACTACCCCA
GCTGCGCAGCAAGCTGGCCTGCAGGGCACTCTCGCCGCTCCTGATGGGGT 4270 4290

CGGTCGCCCACACGATGATCGGCCTCAAGCGTCTGGACAATCTCCACCGG
GCCAGCGGGTGTGCTACTAGCCGGAGTTCGCAGACCTGTTAGAGGTGGCC 4310 4330 4350

TGCCTCGCGGACGTCGTGGAGGACGGCGTCCCCGGTGACTTCATCGAGAC
ACGGAGCGCCTGCAGCACCTCCTGCCGCAGGGGCCACTGAAGTAGCTCTG 4370 4390

CGGGGTGTGCCGCGCGCCGTGCATCTTCGCCCGCGGACTGCTGAACGCGT
GCCCCACACGGCGCGCGGCACGTAGAAGCGGGCGCCTGACGACTTGCGCA 4410 4430 4450

ACGGCCAGGCCGACCGCACCGTCTGGGTCGCCGACTCCTTCCAGGGCTTT
TGCCGGTCCGGCTGGCGTGGCAGACCCAGCGGCTGAGGAAGGTCCCGAAA 4470 4490

CCCGAGCTGACCGGGTCCGACCACCCGCTGGACGTCGAGATCGACCTCCA
GGGCTCGACTGGCCCAGGCTGGTGGGCGACCTGCAGCTCTAGCTGGAGGT 4510 4530 4550

CCAGTACAACGAGGCCGTGGACCAGCCCACCAGCGAGGAGACCGTGCGGG
GGTCATGTTGCTCCGGCACCTGGACGGGTGGACGCTCCTCTGGCACGCCC 4570 4590

AGAACTTCGCCCGGTACGGGCTGCTCGACGACAACGTCCGTTTCCTGGCG
TCTTGAAGCGGGCCATGCCCGACGAGCTGCTGTTGCAGGCAAAGGACCGC 4610 4630 4650

GGGTGGTTCAAGGACACCATGCCGGCTGCGCCCGTGAAGCAGCTCGCGGT
CCCACCAAGTTCCTGTGGTACGGCCGACCGGGGCACTTCGTCGAGCGCCA 4670 4690

GATGCGCCTGGACGGCGACTCCTACGGCGCCACCATGGATGTGCTCGACA
CTACGCGGACCTGCCGCTGAGGATGCCGGCGTGGTACCTACACGAGCTGT 4710 4730 4750

GCCTGTACGAGCGGCTGTCGCCGGGCGGTTTAGTCATCGTCGACGACTAC
CGGACATGCTCGCCGACAGCGGCCCGCCAATGCAGTAGCAGCTGCTGATG 4770 4790

TGCATCCCGGCCTGCCGCGAGCGGTGCACGACTTCCGCGACCGGCTCGGC
ACGTAGGGCCGGACGGCGCTCGCCACGTGCTGAAGGCGCTGGCCGAGCCG 4810 4830 4850

ATCCGCGACACGATCCACCGGATCGACCGCCAGGGCGCTATTGGCGGCAC
TAGGCGCTGTGCTAGGTGGCCTAGCTGGCGGTCCCGCGATAACCGCCGTG 4870 4890

AGCGGCTGAGTCGTTCCGCCCGAGAGCCCGACGAGAGCAGGAGATATGCG
TCGCCGACTCAGCAAGGCGGGCTCGGCCTCTCGGGCTGCCTCTATACGC

-continued

```
4910                 4927

AGACACGCCGCGCCCGCTCGGCATTGA
TCTGTGCTGCGCGGGCGAGCCGTAACT.
```

16. A DNA sequence encoding the *Streptomyces fradiae* tylE gene product, said product comprising the amino acid sequence:

AlaAlaGlyGlySerSerAlaAlaValLeuAlaAspPheAspArgPro-IleTrpGly

ProIleGlyGlyGluSerAsnValGlyLysGluIlePheAlaLeuAsn-HisTyrValHis

LeuGlyValValHisGlyThrProThrAlaProHisAlaAlaThrAsp-GluProLeuGlu

GlnHisGlnLeuSerAspValLeuSerLysValLeuGlyLeuSerThr-LeuAspSerLys

GlyProAspSerAspGlyGlyPheGlyProTrpTyrAlaThrTrpLeu-AspGluIleVal

TyrLeuGlyGlyProArgValHisProPheLeuAlaHisPheSerThr-ArgValHisGlu

AsnIleHisSerGlyAspAspIleValIleAspPheProGlyTyrArg-AlaAlaLeuGlu

ThrLeuCysGlyProAspAsnGlnAspGlyValValThrThrIleArg-GlnGluGluAla

HisSerLysAspGluIleAspLeuGlyTyrIleLeuGlyArgHisPhe-PheHisLysTrp

MetArgLeuSerGlyGlyGlyTrpGluProHisGlnTyrGlyGlyIle-GlyIleGluLeu

ValArgValGluGluAsnArgTyrGluArgPheHisArgAspTyrHis-ProThrPheTrp

HisLeuSerGlyTrpLysProThrLeuTyrArgSerThrLeuGluAsn-LeuAspProLys

AlaSerThrCysGlyAlaLeuValThrAlaThrAlaGlnGlnAlaAla-LeuPheTyrThr

AspIleHisGlyThrGlySerThrAlaTyrProPheLeuThrThrGly-ArgThrGlyAla

AlaArgGluArgCysProGlyPheLeuGluArgValLeuGluAsp-LeuGluTyrGluVal

ArgMetAlaValPheGlyAspAspAspProAlaAlaArgArgVal-ProAlaGlyGlnAla

ValAlaLeuArgArgProValLeuAlaAspGlySerArgValAlaLeu-GluValLeuVal

ProValAspAsnValProHisProAlaArgSerValIleGluAspVal-LeuValAlaThr

ValAlaGluProGlyHisGluAlaValLeuGluArgValAspAlaAla-HisGlyGlyAla

AlaArgIleIleGlnArgValLeuThrAlaGluLysGlnValAlaMet wherein ALA is alanine, ARG is arginine, ASN is asparagine, ASP is aspartic acid, CYS is cysteine, GLN is glutamine, GLU is glutamic acid, GLY is glycine, HIS is histidine, ILE is isoleucine, LEU is leucine, LYS is lysine, MET is methionine, PHE is phenylalanine, PRO is proline, SER is serine, THR is threonine, TRP is tryptophan, TYR is tyrosine, and VAL is valine.

17. The DNA sequence of claim 16 which is

```
    TCACGCGGCACCGCCCGAGGAGGCGGCGACCAGGGCGTCGAAGTCCCGCGGATCCAGCC
 73 -------+---------+---------+---------+---------+---------+-- 132
    AGTGCGCCGTGGCGGGCTCCTCCGCCGCTGGTCCCGCAGCTTCAGGGCGCCCTAGGTCGG

    GGGGATGCCGCCCTCGGAGTTGACCCCCTTCTCGATGAAGGCGAGGTTGTGGTAAACGTG
133 -------+---------+---------+---------+---------+---------+-- 192
    CCCCTACGGCGGGAGCCTCAACTGGGGGAAGAGCTACTTCCGCTCCAACACCATTTGCAC

    CAGGCCCACCACGTGGCCGGTCGGCGTAGCCGGGTGAGCGGCCGTGTCCTCGGGGAGTTC
193 -------+---------+---------+---------+---------+---------+-- 252
    GTCCGGGTGGTGCACCGGCCAGCCGCATCGGCCCACTCGCCGGCACAGGAGCCCCTCAAG

    CTGGTGCTGGAGGCTGTCGACGAGTGACTTCACCAGTCCCAGGCTGGTGAGGTCGCTCTT
253 -------+---------+---------+---------+---------+---------+-- 312
    GACCACGACCTCCGACAGCTGCTCACTGAAGTGGTCAGGGTCCGACCACTCCAGCGAGAA

    GCCGGGGTCCGTGTCGCCGCCGAAGCCGGGCCAGTAGGCGGTCCACAGGTCCTCGATCAC
313 -------+---------+---------+---------+---------+---------+-- 372
    CGGCCCCAGCGACAGCGGCGGCTTCGGCCCGGTCATCCGCCAGGTGTCCAGGAGCTAGTG

    ATACAGCCCGCCGGGCCGCACATGGGGGAAGAGGGCGTGGAAGGAGGTCCGCACATGCTC
373 -------+---------+---------+---------+---------+---------+-- 432
    TATGTCGGGCGGCCCGGCGTGTACCCCCTTCTCCCGCACCTTCCTCCAGGCGTGTACGAG

    GTTGATGTGGCTTCCGTCGTCGATGACGATGTCGAACGGGCCGTAGCGCGCGGCGAGTTC
433 -------+---------+---------+---------+---------+---------+-- 492
    CAACTACACCGAAGGCAGCAGCTACTGCTACAGCTTGCCCGGCATCGCGCGCCGCTCAAG
```

-continued

```
      CGTGAGGCACCCGGGGTCGTTCTGGTCGCCCACCACGGTGGTGATGCGCTGTTCCTCGGC
 493  -------+---------+---------+---------+---------+---------+--  552
      GCACTCCGTGGGCCCCAGCAAGACCAGCGGGTGGTGGCACCACTACGCGACAAGGAGCCG

      GTGTGATTTATCCTCAATGTCCAGGCCGTAGATCAGTCCCCGGTGGAAGAAGTGCTTCCA
 553  -------+---------+---------+---------+---------+---------+--  612
      CACACTAAATAGGAGTTACAGGTCCGGCATCTAGTCAGGGGCCACCTTCTTCACGAAGGT

      CATGCGCAGTGATCCGCCGCCCCACTCGGGGTGCTGGTAGCCGCCTATGCCGATCTCCAG
 613  -------+---------+---------+---------+---------+---------+--  672
      GTACGCGTCACTAGGCGGCGGGGTGAGCCCCACGACCATCGGCGGATACGGCTAGAGGTC

      TACCCGCACCTCCTCGTTGCGGTACTCGCGGAAGTGCCGGTCGTAGTGCGGAGTGAACCA
 673  -------+---------+---------+---------+---------+---------+--  732
      ATGGGCGTGGAGGAGCAACGCCATGAGCGCCTTCACGGCCAGCATCACGCCTCACTTGGT

      GTGGAGCGAGCCCCACTTGGGAGTGAGATAGCGCGAGGTGAGTTCGTTCAGGTCCGGTTT
 733  -------+---------+---------+---------+---------+---------+--  792
      CACGTCGCTCGGGGTGAACCCTCACTCTATCGCGCTCCACTCAAGCAAGTCCAGGCCAAA

      GGCCGAGGTGCAGCCCGCCAGGACGGTGGCCGTCGCCTGCTGCGCCGCGAGGAAGTAGGT
 793  -------+---------+---------+---------+---------+---------+--  852
      CCGGCTCCACGTCGGGCGGTCCTGCCACCGGCAGCGGACGACGCGGCGCTCCTTCATCAA

      GTCGATGTGGCCGGTGCCGGAGGTGGCGTAGGGGAAGAGGGTGGTTCCCCTGGTCCCGGC
 853  -------+---------+---------+---------+---------+---------+--  912
      CAGCTACACCGGCCACGGCCTCCACCGCATCCCCTTCTCCCACCAAGGGGACCAGGGCCG

      GGCCCGCTCCCGGCAGGGGCCAAACAACTCCCGTACCAGTTCGTCGAGTTCGTATTCGAC
 913  -------+---------+---------+---------+---------+---------+--  972
      CCGGGCGAGGGCCGTCCCCGGTTTGTTGAGGGCATGGTCAAGCAGCTCAAGCATAAGCTG

      GCGCATCGCGACAAAGCCGTCGTCATCGGGGGCGGCGCGGCGCACGGGGGCGCCCTGGGC
 973  -------+---------+---------+---------+---------+---------+--  1032
      CGCGTAGCGCTGTTTCGGCAGCAGTAGCCCCCGCCGCGCCGCGTGCCCCCGCGGGACCCG

      GACCGCCAGCCGCCGCGGCACCAGCGCGTCGCCGGACCGTACGGCGAGTTCCACCAGTAC
1033  -------+---------+---------+---------+---------+---------+--  1092
      CTGGCGGTCGGCGGCGCCGTGGTCGCGCAGCGGCCTGGCATGCCGCTCAAGGTGGTCATG

      CGGCACGTCGTTGACCGGGTGCGGCGCCCGGGAGACGATCTCGTCGACCAGGACCGCAGT
1093  -------+---------+---------+---------+---------+---------+--  1152
      GCCGTGCAGCAACTGGCCCACGCCGCGGGCCCTCTGCTAGAGCAGCTGGTCCTGGCGTCA

      CACCGCCTCCGGCCCGTGTTCGGCCACCAGCTCCCGCACATCCGCGGCGTGGCCGCCGGC
1153  -------+---------+---------+---------+---------+---------+--  1212
      GTGGCGGAGGCCGGGCACAAGCCGGTGGTCGAGGGCGTGTAGGCGCCGCACCGGCGGCCG

      CGCCCTGATGATCTGCCGCACCAGAGTGGCCTCTTTCTGCACAGCCAT
1213  -------+---------+---------+---------+---------+  1212
      GCGGGACTACTAGACGGCGTGGTCTCACCGGAGAAAGACGTGTCGGTA.
```

18. A DNA sequence encoding the *Streptomyces fradiae* tylD gene product, said product comprising the amino acid sequence:

SerHisProAlaArgSerProArgHisHisGlyArgTyrTrpArgIle-ThrGlnGlu

IleGlyValArgLeuProArgProGluCysGlyThrValAspArgMet-ArgSerLeuAsp

LeuArgGlnAlaProProGlySerProLysAspProTyrThrArgIle-GlyGlyLysGly

GlyValAlaSerValValThrArgAlaLeuAspLeuIleSerValGlu-GluProSerGly

IleAsnMetValProTyrLysAspAlaGluValMetArgLeuThrAla-AsnValLeuAsp

GluValHisIlePheSerArgThrGlnArgGlyAspGlyTrpIleGlu-IleThrGluGly

AlaAlaAlaArgAlaValMetSerProIleValArgThrArgThrGly-GlyAsnGlyAsp

ArgProGlyTyrValAsnGlyProArgValArgPheIleArgSerGly-PheGluAlaGly

HisLeuGluAlaMet wherein ALA is alanine, ARG is arginine, ASN is asparagine, ASP is aspartic acid, CYS is cysteine, GLN is glutamine, GLU is glutamic acid, GLY is glycine, HIS is histidine, ILE is isoleucine, LEU is leucine, LYS is lysine, MET is methionine, PHE is phenylalanine, PRO is proline, SER is serine, THR is threonine, TRP is tryptophan, TYR is tyrosine, and VAL is valine.

19. The DNA sequence of claim 18 which is

```
     TCACGAGTGGGGTGCCCGCGACGGCCGGTGGTGTCCGCGGTACCAGCGGATGGTCTGCTC
1277 ---+---------+---------+---------+---------+---------+------ 1336
     AGTGCTCACCCCACGGGCGCTGCCGGCCACCACAGGCGCCATGGTCGCCTACCAGACGAG

     GATCCCCACGCGCAGGGGCCTGGGTTCGCAGCCGGTGACGTCACGCATCCGCGACAGGTC
1337 ---+---------+---------+---------+---------+---------+------ 1396
     CTAGGGGTGCGCGTCCCCGGACCCAAGCGTCGGCCACTGCAGTGCGTAGGCGCTGTCCAG

     CAGGCGCTGGGCCGGAGGACCGGAGGGCTTGTCCGGGTAGGTGCGGATGCCTCCCTTCCC
1397 ---+---------+---------+---------+---------+---------+------ 1456
     GTCCGCGACCCGGCCTCCTGGCCTCCCGAACAGGCCCATCCACGCCTACGGAGGGAAGGG

     GCCGACGGCCGAGACCACGGTCCTGGCCAGGTCGAGGATGGACACCTCTTCGGGGGAGCC
1457 ---+---------+---------+---------+---------+---------+------ 1516
     CGGCTGCCGGCTCTGGTGCCAGGACCGGTCCAGCTCCTACCTGTGGAGAAGCCCCCTCGG

     GATGTTCATCACCGGGTACTTGTCCGCCTCGACCATGCGGAGGGTGGCGTTCACCAGGTC
1517 ---+---------+---------+---------+---------+---------+------ 1576
     CTACAAGTAGTGGCCCATGAACAGGCGGAGCTGGTACGCCTCCCACCGCAAGTGGTCCAG

     CTCCACATGGATGAAGGAACGGGTCTGACGGCCGTCCCCCCAGATCTCTATCGTCTCGCC
1577 ---+---------+---------+---------+---------+---------+------ 1636
     GAGGTGTACCTACTTCCTTGCCCAGACTGCCGGCAGGGGGGTCTAGAGATAGCAGAGCGG

     CGCCGCGGCCCGGGCGACCATGCTGGGAATGACCCGGGTGCGGGTTCCGCCGTTCCCGTC
1637 ---+---------+---------+---------+---------+---------+------ 1696
     GCGGCGCCGGGCCCGCTGGTACGACCCTTACTGGGCCCACGCCCAAGGCGGCAAGGGCAG

     CCGGGGCCCGTAGACGTTTCCCGGCCGGACCCGGAAGATCCGGCTGCCGAACTCGGCGCC
1697 ---+---------+---------+---------+---------+---------+------ 1756
     GGCCCCGGGCATCTGCAAAGGGCCGGCCTGGGCCTTCTAGGCCGACGGCTTGAGCCGCGG

     GTGCAGTTCGGCCAT
1757 ---+---------+- 1771
     CACGTCAAGCCGGTA.
```

20. A DNA sequence encoding the *Streptomyces fradiae* tylH gene product, said product comprising the amino acid sequence:

AlaAspArgGlyThrProProAlaAlaAlaGlyAlaGlyAlaGlyThr-GlyAspGly

SerLeuLeuValAlaArgAlaProCysLeuAspGluAlaGluArgVal-GluGluTrpVal

AlaProProProThrArgAspLeuValGlyGlyValGlyAspGluAsp-GlnArgPheVal

ThrproAlaAlaArgGluCysGlnGlyAlaGlyValCysArgGlyThr-AspIleArgVal

ArgMetArgSerGlnGluLysAspAspGluArgGlyAlaThrTrp-TrpAlaValProLeu

GluTyrValGlyPheValAlaSerAspSerLysLeuArgLeuGlyAla-ValAspThrThr

ProArgLeuAlaProLeuArgGluLeuValAlaGlyLeuAlaValGlu-LeuGluMetArg

AlaLeuAsnGlnGlyLeuCysGlnHisProGlyTyrGlyPheAlaVal-HisArgArgAla

SerArgHisIleAspPheAlaGluProGluSerPheValAlaGluAsp-ArgAsnAlaAla

AlaLeuLeuPheValLeuGlyAspGlyAlaArgIleThrHisGlyAsp-IleGluIleAsp

AlaThrAlaSerArgArgLeuGlyAspAlaIleSerLeuTyrArgLeu-LeuGluAspVal

AlaGlyProLeuLeuGlyProAsnValThrLeuGluArgTrpAlaThr-ProHisGlnLeu

LeuValLeuValSerMetThrValMetSerAlaThrThrGluHisGly-AlaAlaLeuLeu

LeuValAlaAsnAspLeuValAspAlaHisSerLeuGlyGlyGly-ArgAlaGlnAlaVal

MetSerGlyLeuMetGlyAspGlySerGluArgGlyThrLysGly-SerIleLeuArgAsp

LeuTyrAspArgLeuGluLeuLeuAlaGluLeuAlaGluGluGly-AlaAlaProArgThr

AlaGlnGluThrArgGluGlnPheTyrAspArgAspGluTyrProIle-AspLeuLeuArg

CysIleValGlnThrAlaMetProLeuAlaPheAspAlaLeuLeuAsp-AlaGluAspGly

ArgAlaThrLeuAspAspLeuLeuGlyThrValIleGlnGluValSer-ProArgLeuGlu

ArgValArgArgLeuGlyPheGluProIlePheHisGlyArgLeuAla-GlyHisAspPro

ProAspLeuThrLeuLeuSerArgSerAlaGluAlaGluGlyAspSer-ProSerLeuArg

ProLeuLysAlaProHisIleSerValArgProAspAlaLeuLeuAla-ArgValHisAsp

GlnArgSerIleLeuTrpValProAlaGlyAspTrpLeuGluAlaArg-AlaIleProGlu

GluAlaArgLeuAlaAlaTyrGlnGluProProSerPheProCysThr-ArgAlaValPro

TrpAlaIleSerArgArgGlyAlaAlaGluAspThrAspAsnAlaArg-AlaAlaProLeu

LeuIleGlyLysGlnSerProArgAlaAspGlySerSerSerVal wherein ALA is alanine, ARG is arginine, ASN is asparagine, ASP is aspartic acid, CYS is cysteine, GLN is glutamine, GLU is glutamic acid, GLY is glycine, HIS is histidine, ILE is isoleucine, LEU is leucine, LSY is lysine, MET is methionine, PHE is phenylalanine, PRO is proline, SER is serine, THR is threonine, TRP is tryptophan, TYR is tyrosine, and VAL is valine.

21. The DNA sequence of claim 20 which is

```
     TCATGCGTCGCGCCCGGTGGGCGGAGCGGCGGCCCCGGCCCCGGCTCCGGTCCCGTCACC
2286 ----+---------+---------+---------+---------+---------+----- 2345
     AGTACGCAGCGCGGGCCACCCGCCTCGCCGCCGGGGCCGGGGCCGAGGCCAGGGCAGTGG

     GGACAGCAGCACGGCACGGGCCGGGCAGAGGTCCTCCGCCTCCCGTACCTCCTCCCATAC
2346 ----+---------+---------+---------+---------+---------+----- 2405
     CCTGTCGTCGTGCCGTGCCCGGCCCGTCTCCAGGAG GCGGAGGGCATGGAGGAGGGTATG

     CGCGGGCGGGGGCGTCCGGTCCAGCACCCCTCCCACGCCGTCCTCGTCCTGCCGGAAGAC
2406 ----+---------+---------+---------+---------+---------+----- 2465
     GCGCCCGCCCCCGCAGGCCAGGTCGTGGGGAGGGTGCGGCAGGAGCAGGACGGCCTTCTG

     GGTGGGCGCCGCCCGCTCGCACTGTCCCGCTCCGACGCAGCGGCCGGTGTCGATCCTCAC
2466 ----+---------+---------+---------+---------+---------+----- 2525
     CCACCCGCGGCGGGCGAGCGTGACAGGGCGAGGCTGCGTCGCCGGCCACAGCTAGGAGTG

     GCGCATCCGTGACTGCTCCTTGTCGTCCTCGCGGCCTGCCGTCCACCAGGCGACGGGCAG
2526 ----+---------+---------+---------+---------+---------+----- 2585
     CGCGTAGGCACTGACGAGGAACAGCAGGAGCGCCGGACGGCAGGTGGTCCGCTGCCCGTC

     CTCGTACACCCCGAAGACCGCGGAGTCGCTCTTGAGCCGCAGCCCGGCGACGTCCGTGGT
2586 ----+---------+---------+---------+---------+---------+----- 2645
     GAGCATGTGGGGCTTCTGGCGCCTCAGCGAGAACTCGGCGTCGGGCCGCTGCAGGCACCA

     CGGCCGCAGTGCGGGCAGCCTCTCCAGCACGGCGCCGAGGGCCACTTCCAGTTCCATCCG
2646 ----+---------+---------+---------+---------+---------+----- 2705
     GCCGGCGTCACGCCCGTCGGAGAGGTCGTGCCGCGGCTCCCGGTGAAGGTCAAGGTAGGC

     GGCGAGGTTCTGTCCCAGGCACTGGTGGGGTCCGTAGCCGAAGGCGACATGCCGCCTCGC
2706 ----+---------+---------+---------+---------+---------+----- 2765
     CCGCTCCAAGACAGGGTCCGTGACCACCCCAGGCATCGGCTTCCGCTGTACGGCGGAGCG

     GGACCGGTGGATGTCGAAGGCCTCCGGTTCGGAGAAGACGGCCTCGTCCCGGTTGGCCGC
2766 ----+---------+---------+---------+---------+---------+----- 2825
     CCTGGCCACCTACAGCTTCCGGAGGCCAAGCCTCTTCTGCCGGAGCAGGGCCAACCGGCG

     GGCCAGCAGGAAGACCAGGCCGTCGCCGGCGCGGATGGTGTGGCCGTCGATCTCGATGTC
2826 ----+---------+---------+---------+---------+---------+----- 2885
     CCGGTCGTCCTTCTGGTCCGGCAGCGGCCGCGCCTACCACACCGGCAGCTAGAGCTACAG

     CGCGGTGGCCGAGCGGCGCAGCCCGTCGGCGATCGACAGATAGCGCAGCAGTTCGTCCAC
2886 ----+---------+---------+---------+---------+---------+----- 2945
     GCGCCACCGGCTCGCCGCGTCGGGCAGCCGCTAGCTGTCTATCGCGTCGTCAAGCAGGTG

     CGCGCCCGGCAACAGGCCGGGATTCACGGTGAGTTCGCGCCAGGCCGTGGGGTGCTGTAG
2946 ----+---------+---------+---------+---------+---------+----- 3005
     GCGCGGGCCGTTGTCCGGCCCTAAGTGCCACTCAAGCGCGGTCCGGCACCCCACGACATC

     CAGAACGAGCACGCTCATCGTGACCATGCTGGCCGTGGTCTCGTGCCCGGCGGCCAGCAG
3006 ----+---------+---------+---------+---------+---------+----- 3065
     GTCTTGCTCGTGCGAGTAGCACTGGTACGACCGGCACCAGAGCACGGGCCGCCGGTCGTC

     GAGCACCGCGTTGTCCAGGACGTCGGCGTGCGACAGCCCGCCACCGCGGGCCTGCGCCAC
3066 ----+---------+---------+---------+---------+---------+----- 3125
     CTCGTGGCGCAACAGGTCCTGCAGCCGCACGCTGTCGGGCGGTGGCGCCCGGACGCGGTG

     CATGCTGCCGAGCATCCCGTCGCCGGATTCCCGGCCGGTCTTGCCGCTGATCAGCCGGTC
3126 ----+---------+---------+---------+---------+---------+----- 3185
     GTACGACGGCTCGTAGGGCAGCGGCCTAAGGGCCGGCCAGAACGGCGACTAGTCGGCCAG

     GAGGTAGTCGCGCAGCTCCAGCAGCGCCTCCAGCGCCTCCTCGCCGGCCGCGGGGCGGGT
3186 ----+---------+---------+---------+---------+---------+----- 3245
     CTCCATCAGCGCGTCGAGGTCGTCGCGGAGGTCGCGGAGGAGCGGCCGGCGCCCCGCCCA

     GGCCTGTTCGGTGCGCTCCTGGAAGTAGTCCCGGTCCTCGTAGGGGATGTCGAGCAGCCG
3246 ----+---------+---------+---------+---------+---------+----- 3305
     CCGGACAAGCCACGCGAGGACCTTCATCAGGGCCAGGAGCATCCCCTACAGCTCGTCGGC

     GCAGATCACCTGGGTCGCCATGGGGAGCGCGAAGTCGGCCAGCAGATCCGCCTCGTCGCC
3306 ----+---------+---------+---------+---------+---------+----- 3365
     CGTCTAGTGGACCCAGCGGTACCCCTCGCGCTTCAGCCGGTCGTCTAGGCGGAGCAGCGG

     GCGGGCGGTGAGGTCATCCAGCAGGCCGGTGACGATCTGTTCGACGGAGGGGCGCAGCTC
```

-continued

```
3366 ----+---------+---------+---------+---------+---------+----- 3425
     CGCCCGCCACTCCAGTAGGTCGTCCGGCCACTGCTAGACAAGCTGCCTCCCCGCGTCGAG

     CCGCACCCGCCGCAGGCCGAACTCGGGGATGAAGTGGCCGCGGAGCGCTCCGTGGTCGGG
3426 ----+---------+---------+---------+---------+---------+----- 3485
     GGCGTGGGCGGCGTCCGGCTTGAGCCCCTACTTCACCGGCGCCTCGCGAGGCACCAGCCC

     CGGGTCCAGTGTCAGCAGCGAACGGGACGCCTCGGCCTCACCGTCGGAGGGTGAGAGCCG
3486 ----+---------+---------+---------+---------+---------+----- 3545
     GCCCAGGTCACAGTCGTCGCTTGCCCTGCGGAGCCGGAGTGGCAGCCTCCCACTCTCGGC

     CGGGAGCTTCGCGGGATGGATGCTGACCCGGGGGTCGGCCAGCAGCGCCCGGACGTGATC
3546 ----+---------+---------+---------+---------+---------+----- 3605
     GCCCTCGAAGCGCCCTACCTACGACTGGGCCCCCAGCCGGTCGTCGCGGGCCTGCACTAG

     CTGGCGGGAGATCAGCCAGACCGGCGCCCCGTCCCACAGCTCGGCCCGGGCGATCGGCTC
3606 ----+---------+---------+---------+---------+---------+----- 3665
     GACCGCCCTCTAGTCGGTCTGGCCGCGGGGCAGGGTGTCGAGCCGGGCCCGCTAGCCGAG

     CTCCGCCCGGAGGGCGGCGTACTGCTCGGGAGGGCTGAAGGGACAGGTGCGGGCGACCGG
3666 ----+---------+---------+---------+---------+---------+----- 3725
     GAGGCGGGCCTCCCGCCGCATGACGAGCCCTCCCGACTTCCCTGTCCACGCCCGCTGGCC

     CCAGGCGATGCTGCGCCGGCCTGCGGCCTCGTCGGTGTCGTTGGCGCGTGCTGCGGGCAA
3726 ----+---------+---------+---------+---------+---------+----- 3785
     GGTCCGCTACGACGCGGCCGGACGCCGGAGCAGCCACAGCAACCGCGCACGACGCCCGTT

     CAGAATCCCCTTTTGTGACGGGCGGGCGTCCCCGGACGAGGACAC
3786 ----+---------+---------+---------+---------+ 3830
     GTCTTAGGGGAAAACACTGCCCGCCCGCAGGGGCCTGCTCCTGTG.
```

22. A DNA sequence encoding the *Streptomyces fradiae* tylJ gene product, said product comprising the amino acid sequence:

TyrArgThrAspArgPheProAlaSerAlaAlaAspValGluGlyLeu-HisTrpArg

AlaLeuGlyLeuValAlaArgThrHisLeuAlaGlyThrAspLeu-AspAspAspValAsp

ProProSerGlyTrpArgArgAlaThrAlaProProAlaAspValLeu-ValValProGly

GlyAspIleHisGlyCysProGlnAlaProGlyGluAspArgGluGly-ValAlaGlyArg

GlnAspIleGluAlaGlyAlaPheValArgGlyProProLeuValGly-AspIleGlyGln

ValGlyIleGluArgAspGlyProGlyLeuValAspLeuGlnGlnGlu-ArgLeuProVal

GlyProArgGlyArgGlnGlyLeuArgArgProAlaProAsnGln-GlyGlyValLeuLeu

ValProLeuValValThrGlnArgArgLeuValGlyProProLeuCys-ArgArgAlaLeu

ProGlyProArgGluAspGluProArgGluProProAlaThrAlaGly-LeuThrValAla

ArgProIleAspProGluArgGlyAlaAlaThrArgArgGlyAlaPro-SerArgGlyGlu

AlaGluArgProVal wherein ALA is alanine, ARG is arginine, ASN is asparagine, ASP is aspartic acid, CYS is cysteine, GLN is glutamine, GLU is glutamic acid, GLY is glycine, HIS is histidine, ILE is isoleucine, LEU is leucine, LYS is lysine, MET is methionine, PHE is phenylalanine, PRO is proline, SER is serine, THR is threonine, TRP is tryptophan, TYR is tyrosine, and VAL is valine.

23. The DNA sequence of claim 22 which is

```
     TCAAATATCGCGTGTCCCGGAAAGGCGCGCTCGCGGCATCCACTTCTCCGAGGTGCCACCG
5046 ----+---------+---------+---------+---------+---------+----- 5105
     AGTTATAGCGCACAGGGCCTTTCCGCGCGAGCGCCGTAGGTGAAGAGGCTCCACGGTGGC

     GGCCAGGCCAAGTACAGCGCGTGTGTGCAGGGCGCCGGTGTCGAGGTCGTCGTCGACATC
5106 ----+---------+---------+---------+---------+---------+----- 5165
     CCGGTCCGGTTCATGTCGCGCACACACGTCCCGCGGCCACAGCTCCAGCAGCAGCTGTAG

     CGGCGGGCTCCCCCACCTACGGGCAGTGGCGGGCGGTGCGTCGACGAGTACAACCGGACC
5166 ----+---------+---------+---------+---------+---------+----- 5225
     GCCGCCCGAGGGGGTGGATGCCCGTCACCGCCCGCCACGCAGCTGCTCATGTTGGCCTGG

     GCCGTCTATGTGCCCGCAGGGCTGGGCCGGGCCTTCGTCGCGCTCACCGACCGCACCACG
5226 ----+---------+---------+---------+---------+---------+----- 5285
     CGGCAGATACACGGGCGTCCCGACCCGGCCCGGAAGCAGCGCGAGTGGCTGGCGTGGTGC

     CTGGTCTTTCTCTGCTCCAGCGAATACGCGGCCCGGCGGGAGCACGCCGTCAATCCCCTG
5286 ----+---------+---------+---------+---------+---------+----- 5345
```

-continued

```
     GACCAGATAGAGACGAGGTCGCTTATGCGCCGGGCCGCCCTCGTGCGGCAGTTAGGGGAC

     GACCCCGATCTCGCGATCGCCTGGCCCGAGGACGTCGAGCTGCTGCTCTCGGAGCGGGAC
5346 ----+---------+---------+---------+---------+---------+----- 5405
     CTGGGGCTAGAGCGCTAGCGGACCGGGCTCCTGCAGCTCGACGACGAGAGCCTCGCCCTG

     ACCCGGGCGCCCACGCTGGCCGAGGCGGCGCGGCGCGGGATTCTGCCCTCCTACCAGGAG
5406 ----+---------+---------+---------+---------+---------+----- 5465
     TGGGCCCGCGGGTGCGACCGGCTCCGCCGCGCCGCGCCCTAAGACGGGAGGATGGTCCTC

     TACCGGGAGCACCACGGTCTGCCGCCGGAGCACGCCCGGCGGTAGGCACCGCCGGGCGAG
5466 ----+---------+---------+---------+---------+---------+----- 5525
   ATGGCCCTCGTGGTGCCAGACGGCGGCCTCGTGCGGGCCGCCATCCGTGGCGGCCCGCTC

     CGGGCCCGGCCGCTCGTCCTCCGGCCGCTCCGGCGGGGCCGTGGCGCCGAGCGTGACGGC
5526 ----+---------+---------+---------+---------+---------+----- 5585
     GCCCGGGCCGGCGAGCAGGAGGCCGGCGAGGCCGCCCCGGCACCGCGGCTCGCACTGCCG

     CCGGGGGATGTCGGGCTCCCGCCCGGCCGCCGTCCTCCGCCCCGCGGGGGACCTGCCCTC
5586 ----+---------+---------+---------+---------+---------+----- 5645
     GGCCCCCTACAGCCCGAGGGCGGGCCGGCGGCAGGAGGCGGGGCGCCCCCTGGACGGGAG

     GGCCTCCCGCGGCAC
5646 ----+---------+ 5660
     CCGGAGGGCGCCGTG.
```

* * * * *